(12) United States Patent
Garcia-Lopez et al.

(10) Patent No.: US 10,351,549 B2
(45) Date of Patent: Jul. 16, 2019

(54) AMIDE DERIVATIVES HAVING MULTIMODAL ACTIVITY AGAINST PAIN

(71) Applicant: ESTEVE PHARMACEUTICALS, S.A., Barcelona (ES)

(72) Inventors: Monica Garcia-Lopez, Barcelona (ES); Carmen Almansa-Rosales, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 15/747,220

(22) PCT Filed: Jul. 28, 2016

(86) PCT No.: PCT/EP2016/001309
§ 371 (c)(1),
(2) Date: Jan. 24, 2018

(87) PCT Pub. No.: WO2017/016668
PCT Pub. Date: Feb. 2, 2017

(65) Prior Publication Data
US 2018/0237415 A1  Aug. 23, 2018

(30) Foreign Application Priority Data
Jul. 29, 2015  (EP) .................................... 15382391

(51) Int. Cl.
| | | |
|---|---|---|
| *A61K 31/397* | (2006.01) | |
| *A61K 31/40* | (2006.01) | |
| *A61K 31/4025* | (2006.01) | |
| *A61K 31/4439* | (2006.01) | |
| *A61P 25/04* | (2006.01) | |
| *A61P 29/00* | (2006.01) | |
| *C07D 205/04* | (2006.01) | |
| *C07D 207/10* | (2006.01) | |
| *C07D 401/12* | (2006.01) | |
| *C07D 211/56* | (2006.01) | |
| *C07D 487/04* | (2006.01) | |

(52) U.S. Cl.
CPC ............ *C07D 401/12* (2013.01); *A61P 25/04* (2018.01); *A61P 29/00* (2018.01); *C07D 211/56* (2013.01); *C07D 487/04* (2013.01); *C07B 2200/07* (2013.01); *C07B 2200/09* (2013.01)

(58) Field of Classification Search
CPC .. A61K 31/397; A61K 31/40; A61K 31/4025; A61K 31/4439; A61P 25/04; A61P 29/00; C07D 205/04; C07D 207/10; C07D 401/12
See application file for complete search history.

(56) References Cited

U.S. PATENT DOCUMENTS

| | | | |
|---|---|---|---|
| 4,229,443 A | 10/1980 | Binderup | |
| 2003/0022891 A1* | 1/2003 | Palani | A61K 31/155 514/227.8 |
| 2006/0148800 A1 | 7/2006 | Stadtmuller | |

FOREIGN PATENT DOCUMENTS

| | | |
|---|---|---|
| DE | 2728588 A1 | 5/1978 |
| EP | 0252670 A2 | 6/1987 |
| WO | WO 03/048154 A1 | 6/2003 |
| WO | WO 2006/021544 A1 | 3/2006 |
| WO | WO 2015/091939 A1 | 6/2015 |

OTHER PUBLICATIONS

Bornot et al., J. Med. Chem, 2013, 56, 1197-1210.
Chien, et al., Neuroscience Letters, 1995, 190, 137-139.
Dickenson, et al., Eur J Pain 9, 113-116 (2005).
Goldberg, et al., BMC Public Health. 11, 770 (2011).
Mao, et al., J. Pain , 12, 157-166 (2011).
Patel, et al., Bioorganic & Medicinal Chemistry Letters, 2008, 18, 5689-5693.
Turk, et al., Lancet, 377, 2226-2235 (2011).
Zamanillo, et al., Eur. J. Pharmacoi, 716, 78-93 (2013).
International Search Report for PCT/EP2016/001309 dated Aug. 30, 2016.

* cited by examiner

*Primary Examiner* — Brenda L Coleman
(74) *Attorney, Agent, or Firm* — Hueschen and Sage

(57) ABSTRACT

The present invention relates to amide derivatives having dual pharmacological activity towards both the sigma (σ) receptor, and the μ-opioid receptor, to processes of preparation of such compounds, to pharmaceutical compositions comprising them, and to their use in therapy, in particular for the treatment of pain.

25 Claims, No Drawings

AMIDE DERIVATIVES HAVING MULTIMODAL ACTIVITY AGAINST PAIN

FIELD OF THE INVENTION

The present invention relates to amide derivatives having dual pharmacological activity towards both the sigma (σ) receptor, and the μ-opioid receptor (MOR or mu-opioid receptor), to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain condictions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies*. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain.

This was mainly achieved by providing the compounds according to the invention that bind both to the µ-opioid receptor and to the $\sigma_1$ receptor.

SUMMARY OF THE INVENTION

In this invention a family of structurally distinct amide derivatives which have a dual pharmacological activity towards both the sigma ($\sigma$) receptor, and the µ-opioid receptor was identified thus solving the above problem of identifying alternative or improved pain treatments by offering such dual compounds.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general Formula (I),

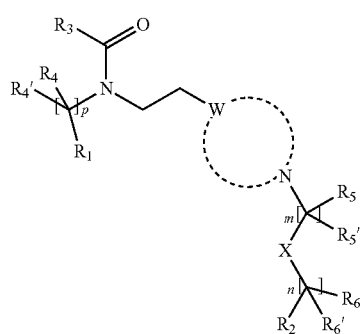

wherein $R_1$, $R_2$, $R_3$, $R_4$, $R_4'$, $R_5$, $R_5'$, $R_6$, $R_6'$, X, W, m, n and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct amide derivatives which have a dual pharmacological activity towards both the sigma ($\sigma$) receptor and the µ-opioid receptor.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to µ-opioid receptor and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of µ-opioid receptor agonists.

A dual compound that possess binding to both the µ-opioid receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and µ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general Formula (I):

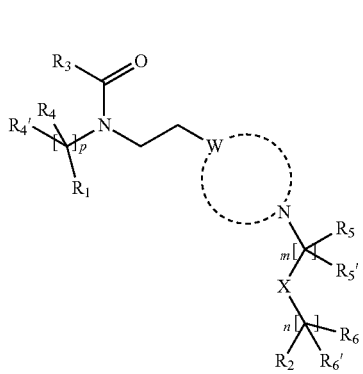

wherein
m is 1 or 2;
n is 0, 1 or 2;
p is 0, 1 or 2;
X is a bond, —C($R_x R_{x'}$)—, C=O or —O—;
  wherein $R_x$ is selected from halogen, —$OR_8$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
W is nitrogen or carbon;
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_7R_{7'}$ and —$CH_2OR_7$;
  wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
$R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

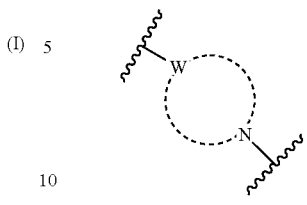

is selected from

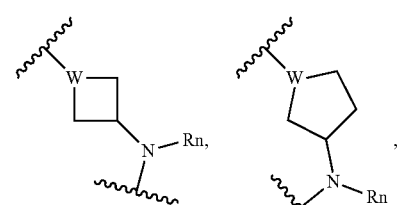

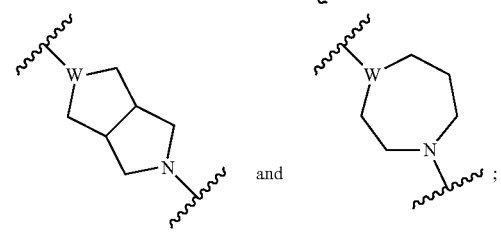

wherein $R_n$ is selected from unsubstituted $C_{1-6}$ alkyl, unsubstituted $C_{2-6}$ alkenyl and unsubstituted $C_{2-6}$ alkynyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment the following proviso applies:
—[$CR_5R_{5'}$]$_m$—X—($CR_6R_{6'}$)$_n$—$R_2$ is not unsubstituted methyl.

In a further embodiment the compound according to the invention of general Formula (I) is a compound of general Formula (I')

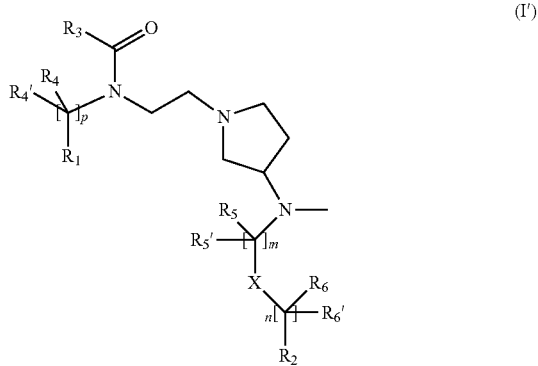

wherein, $R_1$, $R_2$, $R_3$, $R_4$, $R_{4'}$, $R_5$, $R_{5'}$, $R_6$, $R_{6'}$, X, m, n and p are as defined in the description.

In a further embodiment the compound according to the invention of general Formula (I) is a compound of general Formula (I²')

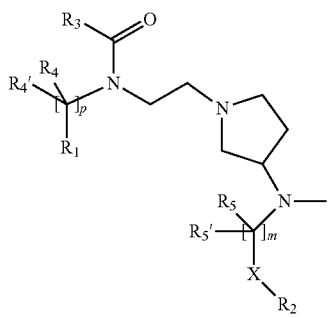

(I²')

wherein $R_1$, $R_2$, $R_3$, $R_4$, $R_4'$, $R_5$, $R_5'$, X, m and p are as defined in the description.

In a further embodiment the compound according to the invention of general Formula (I) is a compound of general Formula (I³')

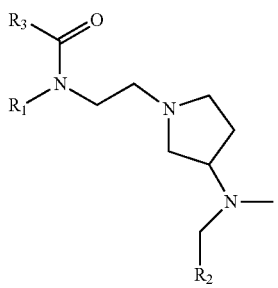

(I³')

wherein $R_1$, $R_2$ and $R_3$ are as defined in the description.

In a further embodiment, for compounds of general Formula (I) described above in which

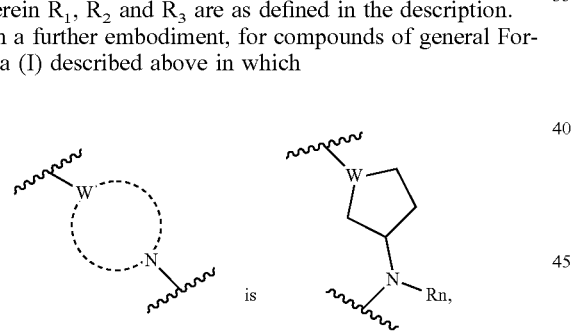

the compounds are thus compounds of general Formula (I⁴')

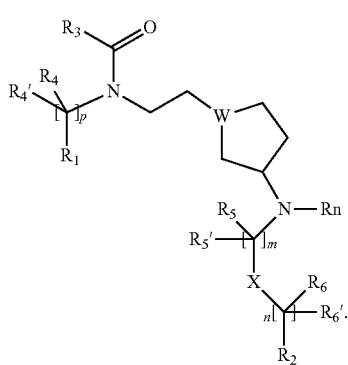

(I⁴')

wherein $R_1$, $R_2$, $R_3$, $R_4$, $R_4'$, $R_5$, $R_5'$, $R_6$, $R_6'$, $R_n$, X, W, m, n and p are as defined in the description.

In a further embodiment, for compounds of general Formula (I) described above in which

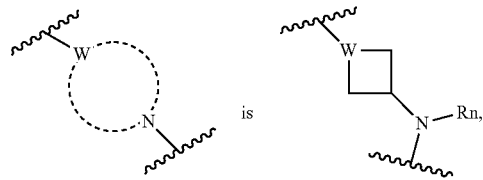

the compounds are thus compounds of general Formula (I⁵')

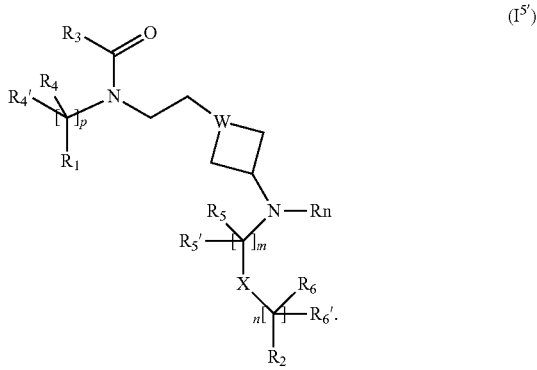

(I⁵')

wherein $R_1$, $R_2$, $R_3$, $R_4$, $R_4'$, $R_5$, $R_5'$, $R_6$, $R_6'$, $R_n$, X, W, m, n and p are as defined in the description.

In a further embodiment, for compounds of general Formula (I) described above in which

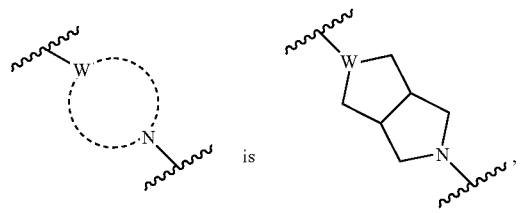

the compounds are thus compounds of general Formula (I⁶')

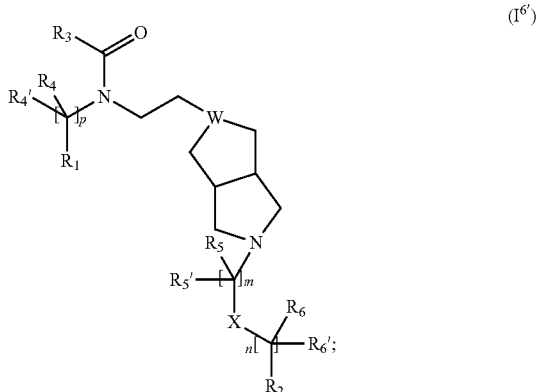

(I⁶')

wherein $R_1$, $R_2$, $R_3$, $R_4$, $R_{4'}$, $R_5$, $R_{5'}$, $R_6$, $R_{6'}$, X, W, m, n and p are as defined in the description.

In a further embodiment, for compounds of general Formula (I) described above in which

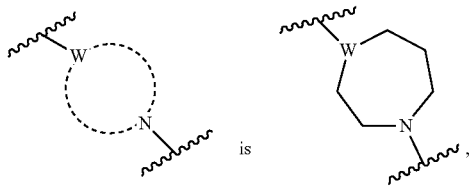

is the compounds are thus compounds of general Formula (I$^{7'}$)

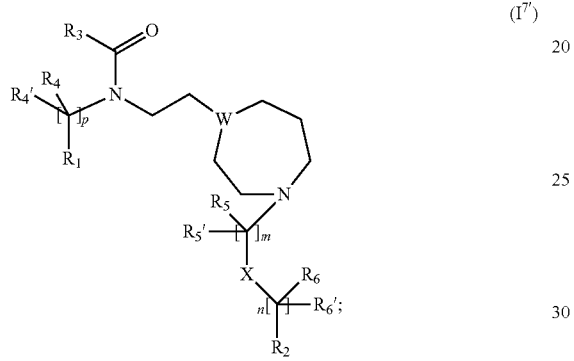

(I$^{7'}$)

wherein $R_1$, $R_2$, $R_3$, $R_4$, $R_{4'}$, $R_5$, $R_{5'}$, $R_6$, $R_{6'}$, X, W, m, n and p are as defined in the description.

For clarity purposes, reference is also made to the following statements below in the definitions of substitutions on alkyl etc. or aryl etc. that "wherein when different radicals $R_1$ to $(R_{13''''})$ $R_{14''''}$ and $R_x$, $R_{x'}$, $R_y$ and $R_n$ are present simultaneously in Formula I they may be identical or different". This statement is thus reflected in the below general Formula (I$^{2a'}$) being derived from and falling into general Formula (I$^{2'}$) as well as Formula (I).

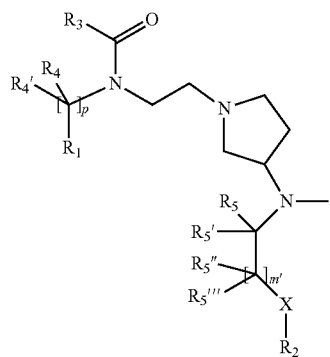

(I$^{2a'}$)

wherein $R_1$, $R_2$, $R_3$, $R_4$, $R_{4'}$, $R_5$, $R_{5'}$, X and p are as defined in the description. In addition, m' (being 0 or 1), $R_{5''}$ and $R_{5'''}$ are added. As said above, this statement is thus reflected in that $R_{5''}$ and $R_{5'''}$ are or could be different from $R_5$ and $R_{5'}$ or not and—accordingly—m' being 0 or 1 is naturally resulting from m (in general Formulas (I) or (I$^2$) being 1 or 2).

The same would be applicable mutatis mutandis for general Formulas like general Formula (I) or general Formula (I') as well as the other general Formulas (I$^{4'}$) to (I$^{7'}$) above.

For clarity purposes, all groups and definitions described in the description and referring to compounds of general Formula (I), also apply to compounds of general Formula (I'), (I$^{2'}$), (I$^{3'}$), (I$^{4'}$), (I$^{5'}$), (I$_6$') or (I$^{7'}$) and also (I$^{2a'}$) when those groups are present in the mentioned general Markush formulae, since compounds of general Formula (I'), (I$^{2'}$), (I$^{3'}$), (I$^{4'}$), (I$^{5'}$), (I$^{6'}$) or (I$^{7'}$) or (I$^{2a'}$) are included in the general Formula (I).

For clarity purposes, the general Markush Formula (I)

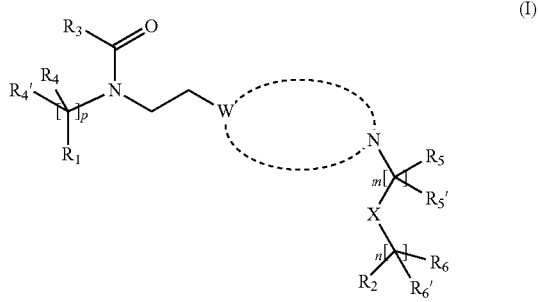

(I)

is equivalent to

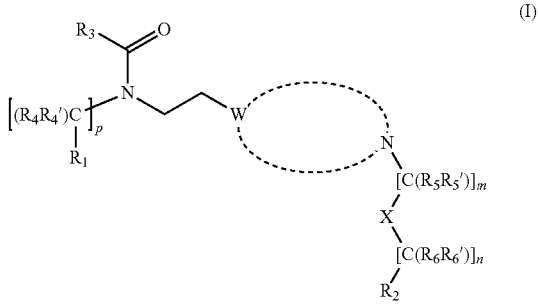

(I)

wherein only —C($R_4R_{4'}$)—, —C($R_5R_{5'}$)— and —C($R_6R_{6'}$)— are included into the brackets and p, m and n mean the number of times that —C($R_4R_{4'}$)—, —C($R_5R_{5'}$)— and —C($R_6R_{6'}$)— are repeated, respectively. The same would apply to general Markush Formulae (I'), (I$^{2'}$), (I$^{2a'}$), (I$^{3'}$), (I$^{4'}$), (I$^{5'}$), (I$^{6'}$) or (I$^{7'}$).

In addition, and for clarity purposes, it should further be understood that naturally if p, m or n are 0, then X, $R_1$ or $R_2$ are still present in general Markush Formulae (I), (I'), (I$^{2'}$), (I$^{2a'}$), (I$^{3'}$), (I$^{4'}$), (I$^{5'}$), (I$^{6'}$) or (I$^{7'}$).

For the sake of clarity the expressions "compound according to Formula (I) . . . , wherein $R_1$, $R_2$, $R_3$, $R_4$, $R_{4'}$, $R_5$, $R_{5'}$, $R_6$, $R_{6'}$, X, m, n and p are as defined in the description" or "compound according to Formula (I) . . . , wherein $R_1$, $R_2$, $R_3$, $R_4$, $R_{4'}$, $R_5$, $R_{5'}$, $R_6$, $R_{6'}$, X, W, m, n and p are as defined in the description" would (just like the expression a "compound of Formula (I) as defined in any one of claims 1 to 11" found in the claims) refer to "a compound according to Formula (I)" (or subformulas like Formula (I')), wherein the definitions of the respective substituents R1 etc. (also from the cited claims) are applied. In addition, this would also mean, though (especially in regards to the claims) that also one or more of the disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims 1 to 11".

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl— unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-6}$alkyl being unsubstituted or substituted by one or more of —$OR_c$ or halogen (F, Cl, I, Br), being $R_c$ represented by $R_{11}$, $R_{12}$, $R_{13}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$), being $R_{c''''}$ represented by $R_{11''''}$, $R_{12''''}$, $R_{13''''}$) wherein $R_1$ to $R_{14''''}$ and $R_x$, $R_{x'}$, $R_y$ and $R_n$ are as defined in the description, and wherein when different radicals $R_1$ to $R_{14''''}$ and $R_x$, $R_{x'}$, $R_y$ and $R_n$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —$OR_c$, —CN, —$SR_c$, —$S(O)R_c$, and —$S(O)_2R_c$, haloalkyl, haloalkoxy or —$OC_{1-6}$alkyl being unsubstituted or substituted by one or more of —$OR_c$ or halogen (F, Cl, I, Br), being $R_c$ represented by $R_{11}$, $R_{12}$, $R_{10}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$, being $R_{c''''}$ represented by $R_{11''''}$, $R_{12''''}$, $R_{13''''}$), wherein $R_1$ to $R_{14''''}$ and $R_x$, $R_{x'}$, $R_y$ and $R_n$ are as defined in the description, and wherein when different radicals $R_1$ to $R_{14''''}$ and $R_x$, $R_{x'}$, $R_y$ and $R_n$ are present simultaneously in Formula I, they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-6}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphtyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered mono or polycyclic heterocyclic ring system of one or more rings of which at least one ring with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane, oxetane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_cR_{c''}$, —$S(O)_2NR_cR_{c'}$, —$NR_cS(O)_2NR_cR_{c''}$, haloalkyl, haloalkoxy, —$SR_c$, —$S(O)R_c$, —$S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$); wherein $R_1$ to $R_{14''''}$ and $R_x$, $R_{x'}$, $R_y$ are as defined in the description, and wherein when different radicals $R_1$ to $R_{14''''}$ and $R_x$, $R_{x'}$, $R_y$ and $R_n$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$, $R_{x'}$ and $R_y$ are as defined in the description, and wherein when different radicals $R_1$ to $R_{14''''}$ and $R_x$, $R_{x'}$, $R_y$ and $R_n$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

or =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein wherein m is 1 or 2;
n is 0, 1 or 2;
p is 0, 1 or 2;
X is a bond, —C($R_x R_{x'}$)—, C═O or —O—;
   wherein $R_x$ is selected from halogen, —$OR_8$, substituted or unsubstituted $C_{1-6}$ alkyl, substituted or unsubstituted $C_{2-6}$ alkenyl and substituted or unsubstituted $C_{2-6}$ alkynyl;
   $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
   $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
W is nitrogen or carbon;
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
   wherein said cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and —$C(CH_3)_2OR_{11}$;
   additionally, cycloalkyl or non-aromatic heterocyclyl in $R_1$, if substituted, may also be substituted with

or ═O;
   wherein the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
   wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
   and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
   wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
   additionally, cycloalkyl or non-aromatic heterocyclyl in $R_2$, if substituted, may also be substituted with

or ═O;
   wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
   wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
   and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_7R_{7'}$ and —$CH_2OR_7$;
   wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, $R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

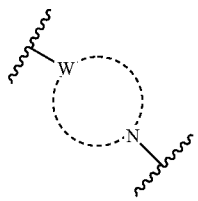

is selected from

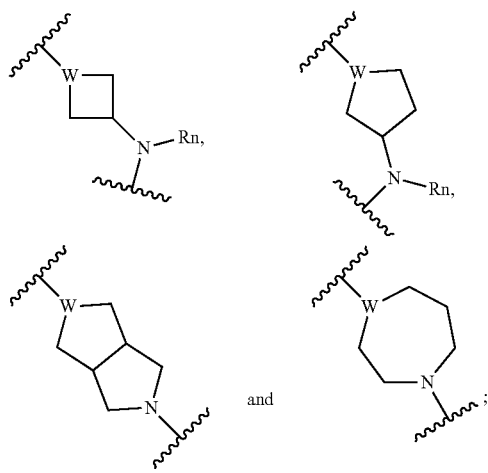

wherein $R_n$ is selected from unsubstituted $C_{1-6}$ alkyl, unsubstituted $C_{2-6}$ alkenyl and unsubstituted $C_{2-6}$ alkynyl;

the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;

wherein $R_{13}$, and $R_{13'}$ are independently selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_3)_2OR_{14}$;

additionally, wherein cycloalkyl or non-aromatic heterocyclyl, other than those defined in $R_1$ or $R_2$, if substituted, may also be substituted with

or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein m is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein p is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is nitrogen or carbon;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is nitrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is carbon;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is a bond, —C($R_x R_{x'}$)—, C=O or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —C($R_x R_{x'}$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is C=O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is substituted or unsubstituted aryl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_7 R_{7'}$ and —$CH_2 OR_7$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ is substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ and $R_7'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, $-OR_8$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, $-OR_8$, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_n$ is selected from unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein is selected from

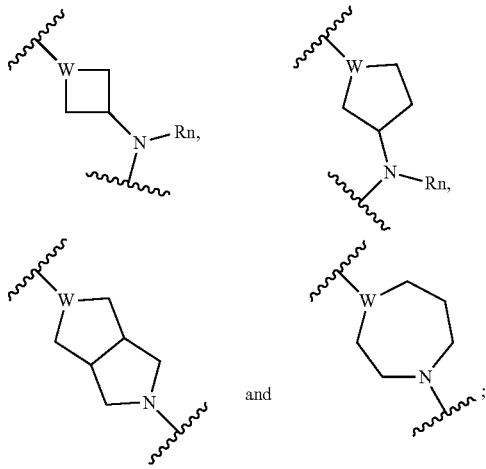

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

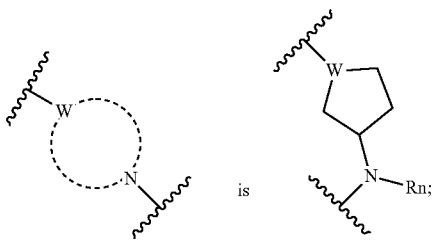

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein
m is 1 or 2; and/or
n is 0, 1 or 2; and/or
p is 0, 1 or 2; and/or
X is a bond, —$C(R_xR_{x'})$—, C=O or —O—; and/or
W is nitrogen or carbon; and/or
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine:
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_7R_{7'}$ and —$CH_2OR_7$;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_5$ and $R_{5'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_7$ and $R_7'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{13}$, and $R_{13'}$ are independently selected from hydrogen, unsubstituted $C_{1-6}$ alkyl, unsubstituted $C_{2-6}$ alkenyl, and unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
the $C_{2-6}$-alkynyl is preferably selected from ethyne, propyne, butyne, pentyne and hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_x$ is selected from halogen, —$OR_8$, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_n$ is selected from unsubstituted $C_{1-6}$ alkyl, unsubstituted $C_{2-6}$ alkenyl and unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl, preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;

and/or
the $C_{2-6}$-alkynyl is preferably selected from ethyne, propyne, butyne, pentyne and hexyne;
and/or
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ and $R_{7'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl; and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13'}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_n$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene; and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene; and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
n is 0, 1 or 2, preferably n is 0;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
m is 1 or 2; preferably m is 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
p is 0, 1 or 2; preferably p is 0;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
X is a bond, —$C(R_xR_{x'})$—, C=O or —O—; preferably, X is a bond or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

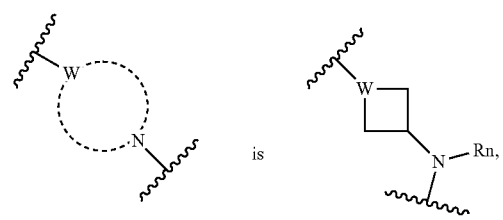

W is nitrogen or carbon; preferably W is nitrogen, and $R_n$ is unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

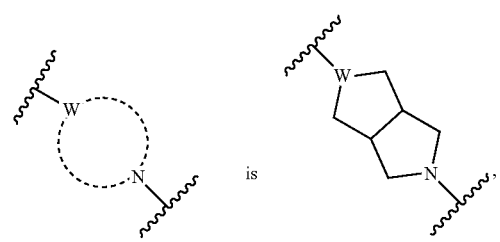

W is nitrogen or carbon; preferably W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

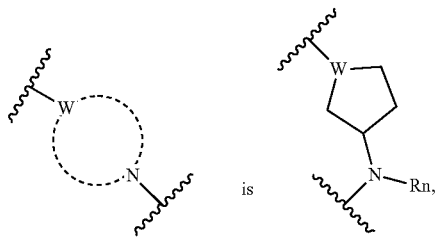

is

W is nitrogen or carbon; preferably W is nitrogen, and $R_n$ is unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I')

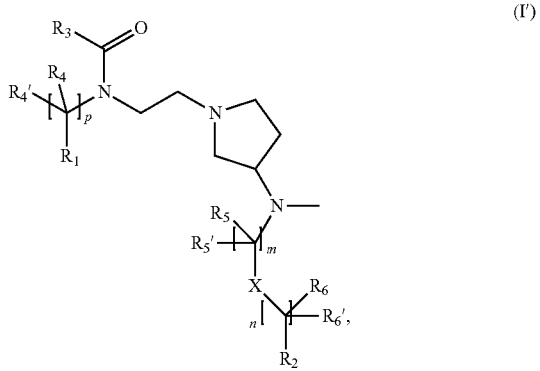

(I')

wherein
m is 1 or 2;
n is 0, 1 or 2;
p is 0, 1 or 2;
X is a bond, —C($R_x R_{x'}$)—, C=O or —O—;
  wherein $R_x$ is selected from halogen, —$OR_8$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11'''}$ and —$C(CH_3)_2OR_{11}$;
  additionally, cycloalkyl or non-aromatic heterocyclyl in $R_1$, if substituted, may also be substituted with

or =O;
  wherein the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
  additionally, cycloalkyl or non-aromatic heterocyclyl in $R_2$, if substituted, may also be substituted with

or =O;
  wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
  wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —NR$_7$R$_{7'}$ and —CH$_2$OR$_7$;
  wherein R$_7$ and R$_7$' are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
R$_4$ and R$_{4'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl,
R$_5$ and R$_{5'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
R$_6$ and R$_{6'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
the alkyl, alkenyl or alkynyl, other than those defined in R$_1$ or R$_2$, if substituted, is substituted with one or more substituent/s selected from —OR$_{13}$, halogen, —CN, haloalkyl, haloalkoxy, —SR$_{13}$, —S(O)R$_{13}$, and —S(O)$_2$R$_{13}$;
  wherein R$_{13}$, and R$_{13'}$ are independently selected from hydrogen, unsubstituted C$_{1-6}$ alkyl, unsubstituted C$_{2-6}$ alkenyl, and unsubstituted C$_{2-6}$ alkynyl;
the aryl, heterocyclyl or cycloalkyl other than those defined in R$_1$ or R$_2$, if substituted, is substituted with one or more substituent/s selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14'''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14'}$R$_{14''}$ and C(CH$_3$)$_2$OR$_{14}$;
additionally, wherein cycloalkyl or non-aromatic heterocyclyl, other than those defined in R$_1$ or R$_2$, if substituted, may also be substituted with

or =O;
  wherein R$_{14}$, R$_{14'}$ and R$_{14''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted cycloalkyl and unsubstituted heterocyclyl;
  and wherein R$_{14'''}$ is selected from hydrogen, unsubstituted C$_{1-6}$ alkyl, unsubstituted C$_{2-6}$ alkenyl, unsubstituted C$_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein
  X is a bond, —C(R$_x$R$_{x'}$)—, C=O or —O—; preferably X is a bond, C=O or —O—; more preferably X is a bond; and/or m is 1 or 2; preferably m is 1; and/or n is 0, 1 or 2; preferably n is 0; and/or p is 0, 1 or 2; preferably p is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein
  X is a bond, —C(R$_x$R$_{x'}$)—, C=O or —O—; preferably X is a bond, C=O or —O—; more preferably X is a bond or —O—; and/or m is 1 or 2; preferably m is 1 or 2; and/or n is 0, 1 or 2; preferably n is 0; and/or p is 0, 1 or 2; preferably p is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{2'}$),

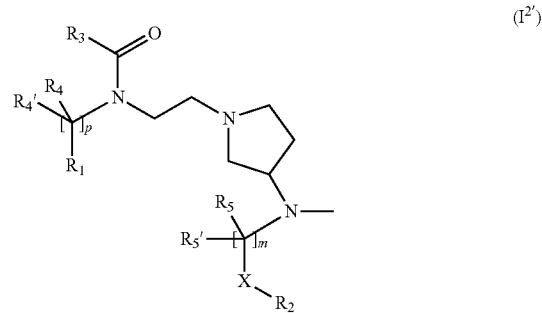

wherein
  X is a bond, —C(R$_x$R$_{x'}$)—, C=O or —O—; preferably X is a bond, C=O or —O—; more preferably X is a bond;

m is 1 or 2; preferably m is 1; and p is 0, 1 or 2; preferably p is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I$^{2a'}$),

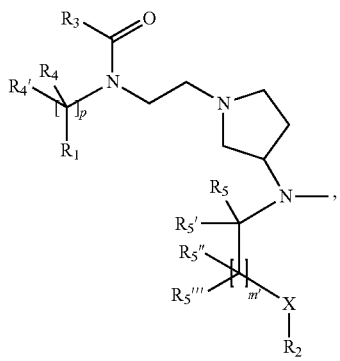

(I$^{2a'}$)

wherein
m' is 0 or 1;
p is 0, 1 or 2;
X is a bond, —C(R$_x$R$_{x'}$)—, C═O or —O—;
  wherein R$_x$ is selected from halogen, —OR$_8$, substituted or unsubstituted C$_{1-6}$ alkyl, substituted or unsubstituted C$_{2-6}$ alkenyl and substituted or unsubstituted C$_{2-6}$ alkynyl;
  R$_{x'}$ is selected from hydrogen, halogen, substituted or unsubstituted C$_{1-6}$ alkyl, substituted or unsubstituted C$_{2-6}$ alkenyl and substituted or unsubstituted C$_{2-6}$ alkynyl;
  R$_8$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
W is nitrogen or carbon;
R$_1$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in R$_1$ if substituted, is substituted with one or more substituent/s selected from halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11'''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —NR$_{11}$S(O)$_2$NR$_{11'}$R$_{11''}$ and —C(CH$_3$)$_2$OR$_{11}$;
  additionally, cycloalkyl or non-aromatic heterocyclyl in R$_1$, if substituted, may also be substituted with

or ═O;
  wherein the alkyl, alkenyl or alkynyl in R$_1$, if substituted, is substituted with one or more substituent/s selected from —OR$_{11}$, halogen, —CN, haloalkyl, haloalkoxy, —SR$_{11}$, —S(O)R$_{11}$, and —S(O)$_2$R$_{11}$;
  wherein R$_{11}$, R$_{11'}$ and R$_{11''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc;
R$_2$ is selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in R$_2$, if substituted, is substituted with one or more substituent/s selected from halogen, —R$_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12'''}$, —SR$_{12}$, —S(O)$_2$R$_{12}$, S(O)$_2$R$_{12}$, —CN, haloalkyl, haloalkoxy, —C(O)OR$_{12}$, —C(O)NR$_{12}$R$_{12'}$, —NR$_{12}$S(O)$_2$NR$_{12'}$R$_{12''}$ and C(CH$_3$)$_2$OR$_{12}$;
  additionally, cycloalkyl or non-aromatic heterocyclyl in R$_2$, if substituted, may also be substituted with

or ═O;
  wherein the alkyl, alkenyl or alkynyl in R$_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;
  wherein R$_{12}$, R$_{12'}$ and R$_{12''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;
R$_3$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —NR$_7$R$_{7'}$ and —CH$_2$OR$_7$;
  wherein R$_7$ and R$_7$' are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
R$_4$ and R$_{4'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl,
R$_5$ and R$_{5'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
R$_{5''}$ and R$_{5'''}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
the alkyl, alkenyl or alkynyl, other than those defined in R$_1$ or R$_2$, if substituted, is substituted with one or more substituent/s selected from —OR$_{13}$, halogen, —CN, haloalkyl, haloalkoxy, —SR$_{13}$, —S(O)R$_{13}$, and —S(O)$_2$R$_{13}$;
  wherein R$_{13}$, and R$_{13'}$ are independently selected from hydrogen, unsubstituted C$_{1-6}$ alkyl, unsubstituted C$_{2-6}$ alkenyl, and unsubstituted C$_{2-6}$ alkynyl;
the aryl, heterocyclyl or cycloalkyl other than those defined in R$_1$ or R$_2$, if substituted, is substituted with one or more substituent/s selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14'''}$, —SR$_{14}$, S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14'}$R$_{14''}$ and C(CH$_3$)$_2$OR$_{14}$;

additionally, wherein cycloalkyl or non-aromatic heterocyclyl, other than those defined in $R_1$ or $R_2$, if substituted, may also be substituted with

or =O;
wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I³'),

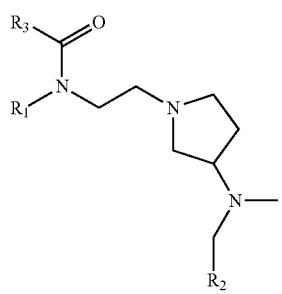

(I³')

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I³') the compound is a compound, wherein
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; preferably $R_1$ is selected from substituted or unsubstituted aryl and substituted or unsubstituted heterocyclyl; more preferably $R_1$ is substituted or unsubstituted phenyl or substituted or unsubstituted pyridine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I³') the compound is a compound, wherein
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; preferably $R_2$ is substituted or unsubstituted aryl; more preferably $R_2$ is substituted or unsubstituted phenyl.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I³') the compound is a compound, wherein
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_7R_{7'}$ and —$CH_2OR_7$; preferably $R_3$ is substituted or unsubstituted ethyl.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from phenyl and pyridine.

In a preferred embodiment
$R_2$ is substituted or unsubstituted phenyl, preferably unsubstituted phenyl.

In a preferred embodiment
$R_2$ is substituted or unsubstituted alkyl, preferably unsubstituted alkyl or alkyl substituted with —O-methyl or substituted with —O-ethyl.

In a preferred embodiment
$R_2$ is substituted or unsubstituted alkyl, preferably unsubstituted alkyl, preferably substituted or unsubstituted methyl, substituted or unsubstituted ethyl or substituted or unsubstituted isopropyl, more preferably unsubstituted methyl, unsubstituted ethyl or unsubstituted isopropyl.

In a preferred embodiment
$R_3$ is substituted or unsubstituted ethyl.

In a preferred embodiment
$R_3$ is unsubstituted ethyl.

In a preferred embodiment
$R_5$ and $R_{5'}$ are both hydrogen.

In a preferred embodiment
X is a bond.

In a preferred embodiment
X is —O—.

In another preferred embodiment
n is 0;

In another preferred embodiment
n is 1.

In another preferred embodiment
m is 1.

In another preferred embodiment
m is 2.

In another preferred embodiment
p is 0.
In an particular embodiment
the halogen is fluorine or chlorine, preferably fluorine.
In a preferred further embodiment, the compounds of the general Formula (I) are selected from

| EX | Chemical name |
|----|---------------|
| 1 | N-(2-(3-(benzyl(methyl)amino)pyrrolidin-1-yl)ethyl)-N-(3-fluoropyridin-2-yl)propionamide |
| 2 | N-(2-(3-(benzyl(methyl)amino)pyrrolidin-1-yl)ethyl)-N-phenylpropionamide |
| 3 | (S)-N-(2-(3-(benzyl(methyl)amino)pyrrolidin-1-yl)ethyl)-N-phenylpropionamide |
| 4 | (R)-N-(2-(3-(benzyl(methyl)amino)pyrrolidin-1-yl)ethyl)-N-phenylpropionamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| | |
|---|---|
| 5 | N-(2-(3-(benzyl(methyl)amino)pyrrolidin-1-yl)ethyl)-N-(6-(trifluoromethyl)pyridin-2-yl)propionamide |
| 6 | Enantiomer of 5 |
| 7 | Enantiomer of 5 |
| 8 | N-(2-(5-benzylhexahydropyrrolo[3,4-c]pyrrol-2(1H)-yl)ethyl)-N-(6-(trifluoromethyl)pyridin-2-yl)propionamide |
| 9 | N-(2-(3-(benzyl(methyl)amino)azetidin-1-yl)ethyl)-N-(6-(trifluoromethyl)pyridin-2-yl)propionamide |
| 10 | N-(2-(3-(isobutyl(methyl)amino)azetidin-1-yl)ethyl)-N-(6-(trifluoromethyl)pyridin-2-yl)propionamide |
| 11 | N-(2-(3-((2-methoxyethyl)(methyl)amino)azetidin-1-yl)ethyl)-N-(6-(trifluoromethyl)pyridin-2-yl)propionamide |
| 12 | N-(2-(3-(isobutyl(methyl)amino)pyrrolidin-1-yl)ethyl)-N-(6-(trifluoromethyl)pyridin-2-yl)propionamide. |
| 13 | Enantiomer of 12 |
| 14 | Enantiomer of 12 |
| 15 | N-(2-(3-((2-ethoxyethyl)(methyl)amino)pyrrolidin-1-yl)ethyl)-N-(6-(trifluoromethyl)pyridin-2-yl)propionamide |
| 16 | Enantiomer of 15 |
| 17 | Enantiomer of 15 |
| 18 | N-(2-(5-isobutylhexahydropyrrolo[3,4-c]pyrrol-2(1H)-yl)ethyl)-N-(6-(trifluoromethyl)pyridin-2-yl)propionamide |
| 19 | N-(2-(5-(2-ethoxyethyl)hexahydropyrrolo[3,4-c]pyrrol-2(1H)-yl)ethyl)-N-(6-(trifluoromethyl)pyridin-2-yl)propionamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein said cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and —$C(CH_3)_2OR_{11}$;
additionally, cycloalkyl or non-aromatic heterocyclyl in $R_1$, if substituted, may also be substituted with

or =O;
wherein the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
additionally, cycloalkyl or non-aromatic heterocyclyl in $R_2$, if substituted, may also be substituted with

or =O;
wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in $R_1$ or $R_2$, if substituted, is substituted with one or more substituent/s selected from $-OR_{13}$, halogen, $-CN$, haloalkyl, haloalkoxy, $-SR_{13}$, $-S(O)R_{13}$, and $-S(O)_2R_{13}$;

wherein $R_{13}$, and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl other than those defined in $R_1$ or $R_2$, if substituted, is substituted with one or more substituent/s selected from halogen, $-R_{14}$, $-OR_{14}$, $-NO_2$, $-NR_{14}R_{14'''}$, $NR_{14}C(O)R_{14'}$, $-NR_{14}S(O)_2R_{14'}$, $-S(O)_2NR_{14}R_{14'}$, $-NR_{14}C(O)NR_{14'}R_{14''}$, $-SR_{14}$, $-S(O)R_{14}$, $S(O)_2R_{14}$, $-CN$, haloalkyl, haloalkoxy, $-C(O)OR_{14}$, $-C(O)NR_{14}R_{14'}$, $-OCH_2CH_2OH$, $-NR_{14}S(O)_2NR_{14'}R_{14''}$ and $C(CH_3)_2OR_{14}$;

additionally, wherein cycloalkyl or non-aromatic heterocyclyl, other than those defined in $R_1$ or $R_2$, if substituted, may also be substituted with

or $=O$;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the cycloalkyl, aryl or heterocyclyl in $R_1$ if substituted, is substituted with one or more substituent/s selected from halogen, $-R_{11}$, $-OR_{11}$, $-NO_2$, $-NR_{11}R_{11'''}$, $NR_{11}C(O)R_{11'}$, $-NR_{11}S(O)_2R_{11'}$, $-S(O)_2NR_{11}R_{11'}$, $-NR_{11}C(O)NR_{11'}R_{11''}$, $-SR_{11}$, $-S(O)R_{11}$, $S(O)_2R_{11}$, $-CN$, haloalkyl, haloalkoxy, $-C(O)OR_{11}$, $-C(O)NR_{11}R_{11'}$, $-NR_{11}S(O)_2NR_{11'}R_{11''}$ and $-C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the cycloalkyl or non-aromatic heterocyclyl in $R_1$, if substituted, may also be substituted with

or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the alkyl, alkenyl or alkynyl in $R_1$, if substituted, is substituted with one or more substituent/s selected from $-OR_{11}$, halogen, $-CN$, haloalkyl, haloalkoxy, $-SR_{11}$, $-S(O)R_{11}$, and $-S(O)_2R_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl, aryl or heterocyclyl in $R_2$, if substituted, is substituted with one or more substituent/s selected from halogen, $-R_{12}$, $-OR_{12}$, $-NO_2$, $-NR_{12}R_{12'''}$, $NR_{12}C(O)R_{12'}$, $-NR_{12}S(O)_2R_{12'}$, $-S(O)_2NR_{12}R_{12'}$, $-NR_{12}C(O)NR_{12'}R_{12''}$, $-SR_{12}$, $-S(O)R_{12}$, $S(O)_2R_{12}$, $-CN$, haloalkyl, haloalkoxy, $-C(O)OR_{12}$, $-C(O)NR_{12}R_{12'}$, $-NR_{12}S(O)_2NR_{12'}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl or non-aromatic heterocyclyl in $R_2$, if substituted, may also be substituted with

or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$ or $R_2$ of any of the embodiments of the present invention,
the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$ or $R_2$ of any of the embodiments of the present invention, the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14'''}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_3)_2OR_{14}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to to the cycloalkyl, aryl or heterocyclyl other than those defined in $R_1$ or $R_2$ of any of the embodiments of the present invention, the cycloalkyl or non-aromatic heterocyclyl, other than those defined in $R_1$ or $R_2$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the halogen is fluorine, chlorine, iodine or bromine, preferably fluorine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)
the halogen is fluorine or chlorine, preferably fluorine:
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the haloalkyl is —$CF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I),
the haloalkoxy is —$OCF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the $\sigma_1$ receptor and the μ-opioid receptor it is a very preferred embodiment in which the compounds are selected which act as dual ligands of the $\sigma_1$ receptor and the μ-opioid receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general Formula (I), (I'), ($I^{2'}$), ($I^{3'}$), ($I^{4'}$), ($I^{5'}$), ($I^{6'}$) or ($I^{7'}$) or ($I^{2a'}$).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I), following scheme 1.

A preferred embodiment of the invention is a process for the production of a compound according to Formula (I), wherein $R_1$, $R_2$, $R_3$, $R_4$, $R_{4'}$, $R_5$, $R_{5'}$, $R_6$, $R_{6'}$, X, W, m, n and p are as defined in the description, following scheme 1.

In all processes and uses described underneath and in scheme 1, the values of $R_1$, $R_2$, $R_3$, $R_4$, $R_{4'}$, $R_5$, $R_{5'}$, $R_6$, $R_{6'}$, X, W, m, n and p are as defined in the description, L is a leaving group such as halogen, mesylate, tosylate or triflate, Z is chloro, bromo, hydroxy, methoxy or ethoxy, Y is

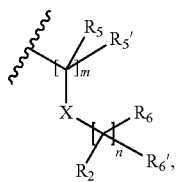

and PG is a protecting group, such as benzyl and tert-butoxycarbonyl.

In a particular embodiment there is a process for the production of a compound of Formula (I),

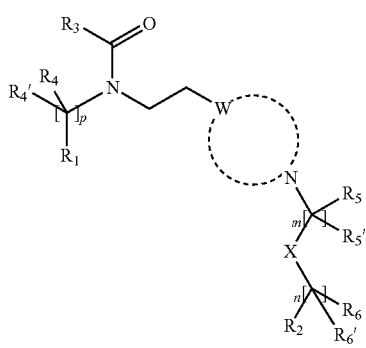 (I)

said process comprises reacting a compound of Formula VII

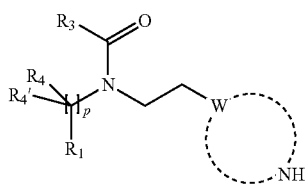 VII with a compound of formula VIIIa through an alkylaton reaction or VIIIb through a reductive amination reaction following STEP 4 of scheme 1

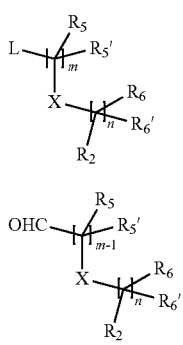

VIIIa

VIIIb

In a particular embodiment there is a process for the production of a compound of Formula (I),

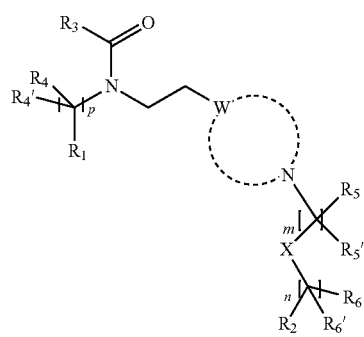 (I)

said process comprises an acylation of a compound of Formula IVb

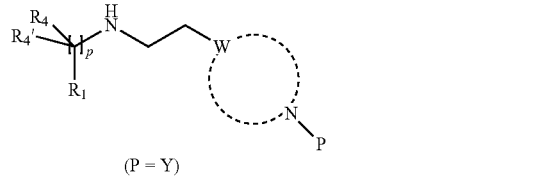 IVb (P = Y)

with a compound of formula Va or Vb following STEP 2 of scheme 1

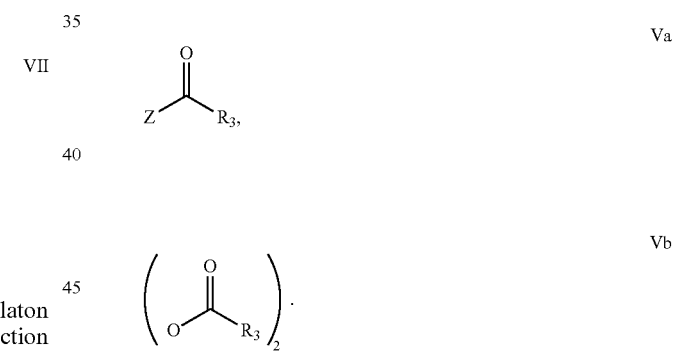

Va

Vb

In a particular embodiment there is a process for the production of a compound of Formula VII,

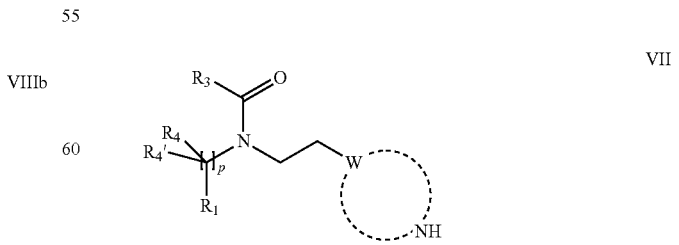 VII said process comprises a deprotection reaction of a compound of Formula VI following STEP 3 of scheme 1

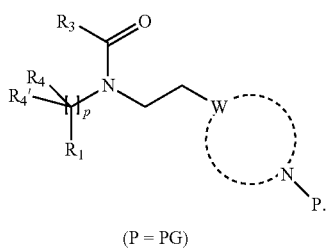

(P = PG)

In a particular embodiment there is a process for the production of a compound of Formula VI,

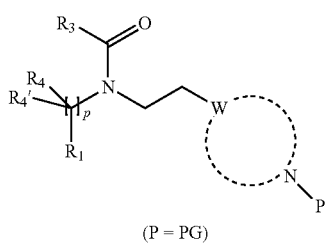

(P = PG)

said process comprises an acylation of a compound of Formula IVa

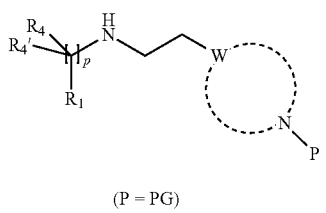

(P = PG)

with a compound of formula Va or Vb following STEP 2 of scheme 1

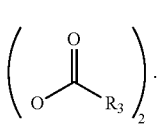

In a particular embodiment there is a process for the production of a compound of Formula Va or Vb,

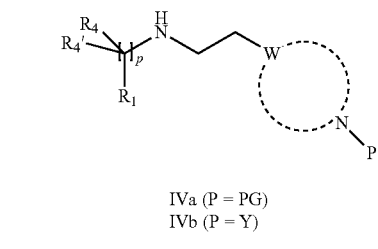

IVa (P = PG)
IVb (P = Y)

said process comprises reacting a compound of Formula IIa or IIb, respectively

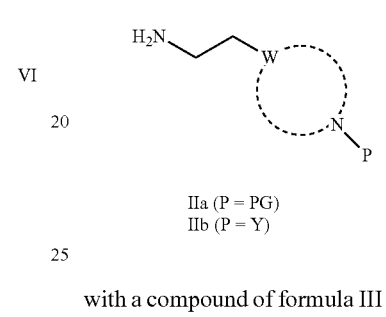

IIa (P = PG)
IIb (P = Y)

with a compound of formula III following STEP 1 of scheme 1

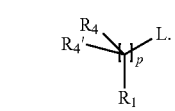

In another particular embodiment a compound of Formula (IIa) or (IIb),

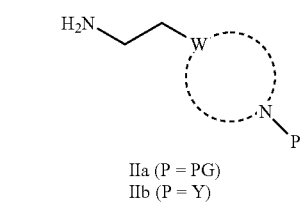

IIa (P = PG)
IIb (P = Y)

is used for the preparation of a compound of Formula (I).

In another particular embodiment a compound of Formula (III),

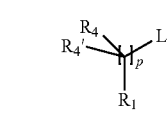

is used for the preparation of a compound of Formula (I).

In another particular embodiment a compound of Formula (IVa) or (IVb),

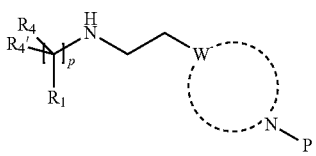

IVa (P = PG)
IVb (P = Y)

is used for the preparation of a compound of Formula (I).

In another particular embodiment a compound of Formula (Va) or (Vb),

Va

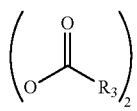

Vb is used for the preparation of a compound of Formula (I).

In another particular embodiment a compound of Formula (VI),

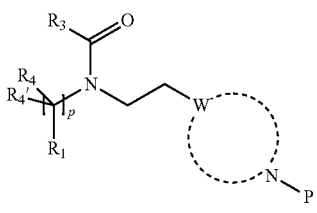

VI (P = PG)

is used for the preparation of a compound of Formula (I).

In another particular embodiment a compound of Formula (VII),

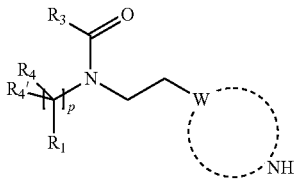

VII is used for the preparation of a compound of Formula (I).

In another particular embodiment a compound of Formula (VIIIa) or (VIIIb),

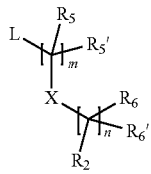

VIIIa

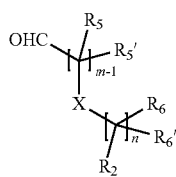

VIIIb is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art.

The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A process is described in Scheme 1 for the preparation of compounds of general formula I, wherein $R_1$, $R_2$, $R_3$, $R_4$, $R_{4'}$, $R_5$, $R_{5'}$, $R_6$, $R_{6'}$, W and X have the meanings defined above.

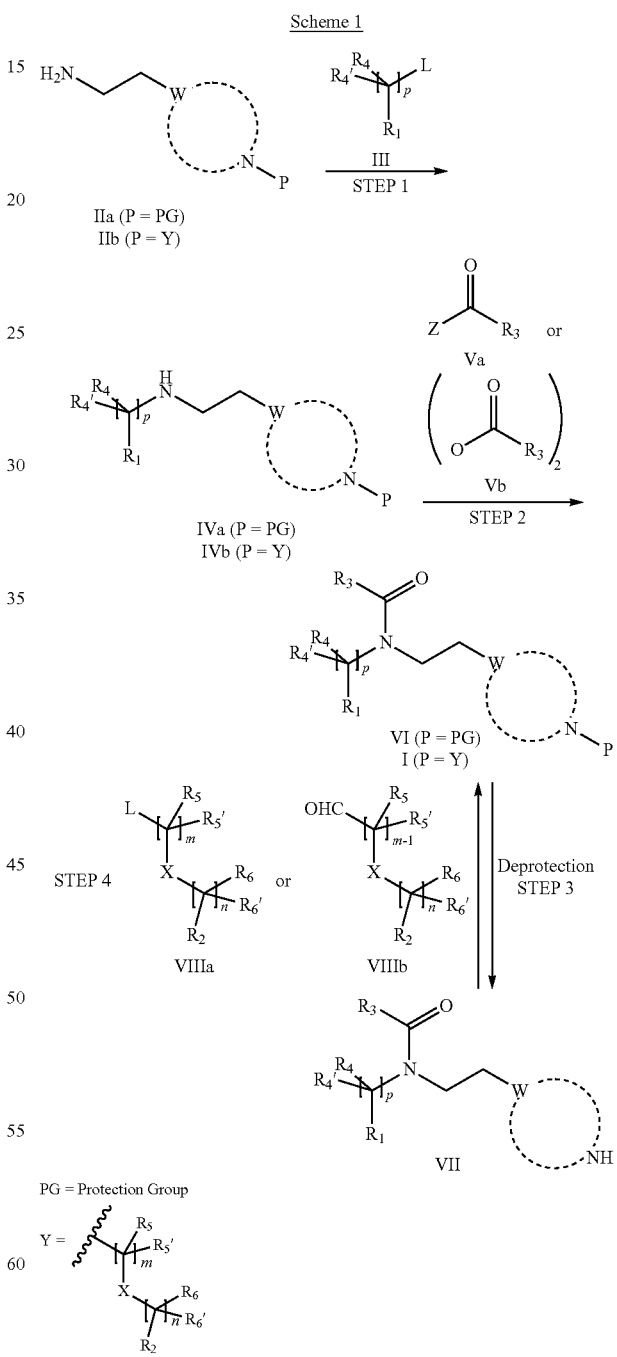

Where, L is a leaving group such as halogen, mesylate, tosylate or triflate and Z is chloro, bromo, hydroxy, methoxy or ethoxy, Y is the group indicated in a square in Scheme 1 and PG is a protecting group, such as benzyl or tert-butoxycarbonyl.

This process is carried out as described below:

Step 1: The compounds of formula IVa or IVb are prepared by reacting a compound of formula IIa or IIb, respectively, with a compound of formula III. Depending on the meaning of p and $R_1$, different reaction conditions will apply:

a) When p is 0 and $R_1$ is aryl or heterocyclyl, compound III is an arylating agent and L represents halogen (preferably bromo or iodo) or triflate. This arylation reaction is carried out under catalytic conditions using a palladium or copper catalyst, in the presence of a suitable ligand and a suitable base, in a suitable solvent, and at a suitable temperature, preferably heating at the reflux temperature or in a microwave reactor. When using copper catalysts such as copper iodide, L-proline is the preferred ligand, potassium phosphate is used preferably as the base and dimethylsulfoxide is the solvent of choice. When using palladium catalysts, such as tris(dibenzylideneacetone)dipalladium or palladium diacetate, 4, 5-bis(diphenylphosphino)-9,9-dimethylxanthene (XAMPHOS) or 2,2'-is(diphenylphosphino)-1,1'-binaphthyl (BINAP) are the preferred ligands, cessium carbonate or sodium tert-butoxide are used preferably as the base and 1,4-dioxane or toluene are the solvents of choice.

b) When p is 1 or 2, compound III is an alkylating agent and L represents a leaving group such as halogen, mesylate, tosylate or triflate. The alkylation reaction is carried out in a suitable solvent, such as acetonitrile, dichloromethane, 1,4-dioxane or dimethylformamide, preferably in acetonitrile, in the presence of an inorganic base such as $K_2CO_3$ or $Cs_2CO_3$, or an organic base such as triethylamine or diisopropylethylamine, preferably $K_2CO_3$, at a suitable temperature comprised between room temperature and the reflux temperature, preferably heating, or alternatively, the reactions can be carried out in a microwave reactor. Additionally, an activating agent, such as NaI, can be used.

Step 2: Compounds of general formula VI or I are prepared by acylation of the NH group of compounds IVa or IVb. The acylating agent can be an acyl halide of formula Va or an anhydride of formula Vb, and the reaction is carried out in the presence of a suitable solvent, such as acetonitrile, dichloromethane, 1,4-dioxane, 1,2-dicloroethane, toluene or dimethylformamide, in the presence of an organic base such as triethylamine, pyridine or diisopropylethylamine, at a suitable temperature comprised between room temperature and the reflux temperature, or alternatively, the reactions can be carried out in a microwave reactor.

For compounds of general formula VI, wherein P is a protecting group, two additional steps are necessary to obtain compounds of formula I:

Step 3: A compound of formula VII is prepared by deprotection reaction of a compound of formula VI. Deprotection is effected in different conditions depending of the protecting group. If the protecting group is benzyl the deprotection is carried out under hydrogenation conditions, at a pressure comprised between 1 and 10 bars, in the presence of Pd, in a suitable solvent such as methanol or ethanol, at a suitable temperature comprised between room temperature and the reflux temperature, preferably at the reflux temperature. If the protecting group is tert-butoxycarbonyl, the deprotection is carried out in the presence of an inorganic acid such as HCl or trifluoroacetic acid, preferably trifluoroacetic acid, in a suitable solvent such as dichloromethane, at a suitable temperature comprised between room temperature and the reflux temperature, preferably at room temperature.

Step 4: From deprotected compounds of formula VII, compounds of general formula I can be prepared by reaction with suitable reagents, such as those of formula VIIIa-b, using different conditions depending on the reagent nature. Thus:

The alkylation reaction with a compound of formula VIIIa is carried out in a suitable solvent, such as acetonitrile, dichloromethane, 1,4-dioxane or dimethylformamide, preferably in acetonitrile, in the presence of an inorganic base such as $K_2CO_3$ or $Cs_2CO_3$, or an organic base such as triethylamine or diisopropylethylamine, preferably diisopropylethylamine, at a suitable temperature comprised between room temperature and the reflux temperature, preferably heating, or alternatively, the reactions can be carried out in a microwave reactor. Additionally, an activating agent, such as NaI, can be used.

The reductive amination with a compound of formula VIIIb, is carried out in the presence of a reductive reagent, preferably sodium triacetoxyborohydride, in a suitable solvent, preferably methanol, at a suitable temperature comprised between room temperature and the reflux temperature, preferably in a microwave reactor.

The process described by Steps 1 to 4 represents the general route for the preparation of compounds of formula I. Additionally, the functional groups present in any of the positions can be interconverted using reactions known to those skilled in the art.

Compounds of formula II, III, V and VIII where $R_1$, $R_2$, $R_3$, $R_4$, $R_{4'}$, $R_5$, $R_{5'}$, $R_6$, $R_{6'}$, W and X have the meanings as defined above, are commercially available or can be prepared by conventional methods described in the bibliography. The preparation of compounds II wherein W is nitrogen, involves the alkylation of a conveniently substituted diamine compound with adequate protected or substituted halide alkyl amines in the conditions previously described in step 4.

EXAMPLES

Intermediates and Examples

The following abbreviations are used in the examples:
AcOEt: Ethyl acetate
BINAP: 2,2'-Bis(diphenylphosphino)-1,1'-binaphthyl
Conc: Concentrated
CH: Cyclohexane
DCM: Dichloromethane
DIPEA: N,N-Diisopropylethylamine
EtOH: Ethanol
Ex: Example
h: Hour/s
HPLC: High-performance liquid chromatography
INT: Intermediate
MeOH: Methanol
MS: Mass spectrometry
Min: Minutes
Quant: Quantitative
Ret: Retention
rt: Room temperature
Sat: Saturated
TEA: $Et_3N$, Triethylamine
TFA: Trifluoroacetic acid
THF: Tetrahydrofuran
Wt: Weight The following method was used to obtain the HPLC-MS data:

A: Column Acquity UPLC BEH C18 2.1×50 mm, 1.7 μm; flow rate 0.61 mL/min; A: NH₄HCO₃ 10 mM; B: ACN; Gradient: 0.3 min in 98% A, 98% A to 5% A in 2.7 min, 2 min in 0% A, 0% A to 98% A in 0.2 min, 0.55 min in 98% A B: Column: Aqcuity BEH C18 2.1×50 mm 1.7 μm; flow rate 800 μl/min; A: NH4HCO3 10 mM; B: ACN; Gradient: 0.3 min in 90% A, 90% A to 5% A in 2.7 min, 0.7 min in 5% A, 5% A to 90% A in 0.1 min, 1.2 min in 90% A Intermediate 1. tert-Butyl 3-(methylsulfonyloxy)pyrrolidine-1-carboxylate

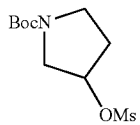

Et₃N (5.58 mL, 40 mmol) was added to a solution of tert-butyl 3-hydroxypyrrolidine-1-carboxylate (3 g, 16.02 mmol) in dry DCM (35 mL). The solution was cooled to 0° C., stirred for 10 min and then, methanesulfonyl chloride (2.1 mL, 27.24 mmol) was added and the reaction mixture was stirred at 0° C. After 1 h the reaction mixture was allowed to warm to rt and stirred for 0.5 h. The mixture was poured into ice-water and diluted with DCM. The organic layer was washed with water, dried over Na₂SO₄, filtered and evaporated to dryness to afford the title compound as yellow oil (4.25 g, yield 99%) that was used in the next step without further purification.

¹H NMR (400 MHz, CDC13) δ ppm 1.49 (s, 9H) 2.08-2.21 (m, 1H) 2.29 (br. s., 1H) 3.07 (s, 3H) 3.36-3.64 (m, 3H) 3.65-3.75 (m, 1H) 5.28 (tt, J=4.23, 2.08 Hz, 1H))

Intermediate 2. tert-Butyl 3-(benzyl(methyl)amino)pyrrolidine-1-carboxylate

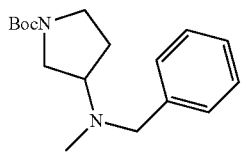 [SMILES: CN(Cc1ccccc1)C1CCN(C(=O)OC(C)(C)C)C1]

A mixture of tert-butyl 3-(methylsulfonyloxy)pyrrolidine-1-carboxylate (INT 1, 4.25 g, 16.02 mmol)) and N-Methyl-1-phenylmethanamine (6.20 mL, 48.07 mmol) was stirred and heated at 100° C. for 3 h, under nitrogen. The residue was portioned between DCM/water. The aqueous phase was further extracted with dichloromethane. The combined extracts were washed with brine and dried (Na₂SO₄) filtered and evaporated. The crude product thus obtained was purified by flash chromatography on silica gel, gradient CH:AcOEt from (100:0) to (70:30) to give the title compound as yellow oil (2.93 g, 63% yield).

HPLC-MS (Method A): Ret, 2.20 min; ESI+–MS m/z, 291 (M+1).

Intermediate 3. N-Benzyl-N-methylpyrrolidin-3-amine

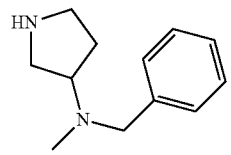

Over a suspension of tert-butyl 3-(benzyl(methyl)amino)pyrrolidine-1-carboxylate (INT 2, 2.5 g, 8.71 mmol) in DCM (20 mL), TFA (16.7 mL, 218 mmol) was added and the mixture was stirred at rt for 1 h. The solvent was concentrated off. The crude residue was diluted with H₂O (30 mL), taken up to pH 12 with 10% aqueous NaOH solution and extracted with DCM (30 mL). The combined organic layers were dried over Na₂SO₄, filtered and concentrated to give the title compound as brown oil (1.66 g, quant yield).

HPLC-MS (Method A): Ret, 1.01 min; ESI+–MS m/z, 191 (M+1).

Intermediate 4A. tert-Butyl 2-(3-(benzyl(methyl)amino)pyrrolidin-1-yl)ethylcarbamate

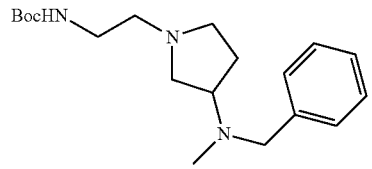 [SMILES: CN(Cc1ccccc1)C1CCN(CCNC(=O)OC(C)(C)C)C1]

tert-Butyl 2-bromoethylcarbamate (0.71 g, 3.15 mmol) was added to a solution of N-benzyl-N-methylpyrrolidin-3-amine (INT 3, 0.4 g, 2.1 mmol) and DIPEA (0.73 mL, 4.2 mmol) in ACN (15 mL). The reaction mixture was stirred at 60° C. overnight and then it was cooled down to rt. The solvent was concentrated in vacuo and the residue was partitioned between AcOEt and sat aqueous NaHCO₃ solution. The organic layer was separated, dried over Na₂SO₄, filtered and concentrated. The crude product thus obtained was purified by flash chromatography on silica gel, gradient DCM:MeOH from (100:0) to (70:30) to give the title compound (0.42 g, 60% yield).

HPLC-MS (Method A): Ret, 1.84 min; ESI+–MS m/z, 334 (M+1).

This method was used for the preparation of intermediates 4B-4E using suitable starting materials:

| INT | Structure | Chemical name | Method | Ret (min) | MS (M + H) |
|---|---|---|---|---|---|
| 4B | 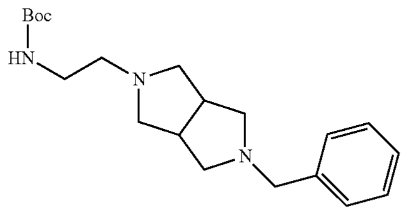 [SMILES: CC(C)(C)OC(=O)NCCN1CC2CN(Cc3ccccc3)CC2C1] | tert-butyl (2-(5-benzylhexahydro-pyrrolo[3,4-c]pyrrol-2(1H)-yl)ethyl)carbamate | B | 1.89 | 346 |
| 4C | 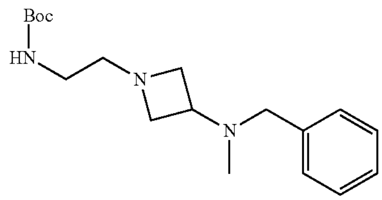 [SMILES: CN(Cc1ccccc1)C1CN(CCNC(=O)OC(C)(C)C)C1] | tert-butyl (2-(3-(benzyl(methyl)amino)azetidin-1-yl)ethyl)carbamate | A | 1.75 | 320 |
| 4D | 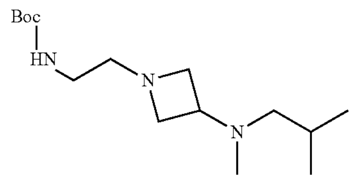 [SMILES: CC(C)CN(C)C1CN(CCNC(=O)OC(C)(C)C)C1] | tert-butyl (2-(3-(isobutyl(methyl)amino)azetidin-1-yl)ethyl)carbamate | A | 1.75 | 286 |
| 4E | 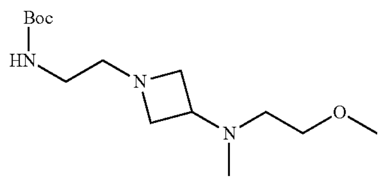 [SMILES: COCCN(C)C1CN(CCNC(=O)OC(C)(C)C)C1] | tert-butyl (2-(3-((2-methoxyethyl)(methyl)amino)azetidin-1-yl)ethyl)carbamate | A | 1.36 | 302 |

Intermediate 5A. 1-(2-Aminoethyl)-N-benzyl-N-methylpyrrolidin-3-amine

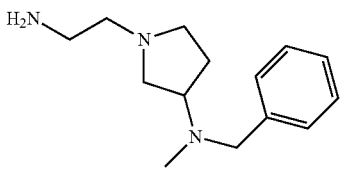 [SMILES: CN(Cc1ccccc1)C1CCN(CCN)C1]

Over a suspension of tert-butyl 2-(3-(benzyl(methyl)amino)pyrrolidin-1-yl)ethylcarbamate (INT 4A, 0.42 g, 1.26 mmol) in DCM (6 mL), TFA (2.36 mL, 30.86 mmol) was added and the mixture was stirred at rt for 4 h. The solvent was concentrated off. The crude residue was diluted with H₂O (5 mL), taken up to pH 12 with 10% aqueous NaOH solution and extracted with DCM (10 mL). The combined organic layers were dried over Na₂SO₄, filtered and concentrated to give the title compound as oil (0.26 g, yield 90%).

HPLC-MS (Method A): Ret, 1.12 min; ESI+-MS m/z, 234 (M+1).

This method was used for the preparation of intermediates 5B-5E using intermediates 4B-4E as starting materials:

| INT | Structure | Chemical name | Method | Ret (min) | MS (M + H) |
|---|---|---|---|---|---|
| 5B | 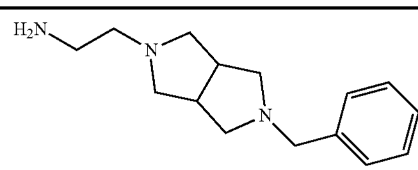 | 2-(5-benzylhexahydro-pyrrolo[3,4-c]pyrrol-2(1H)-yl)ethanamine | A | 1.17 | 246 |
| 5C | 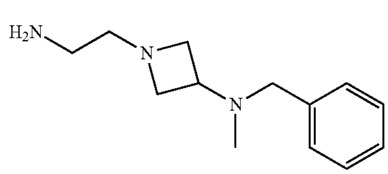 [SMILES: CN(Cc1ccccc1)C1CN(CCN)C1] | 1-(2-aminoethyl)-N-benzyl-N-methylazetidin-3-amine | A | 1.10 | 220 |

-continued

| INT | Structure | Chemical name | Method | Ret (min) | MS (M + H) |
|---|---|---|---|---|---|
| 5D | H₂N–⟨azetidine⟩–N(CH₃)–CH₂CH(CH₃)₂ | 1-(2-aminoethyl)-N-isobutyl-N-methylazetidin-3-amine | A | 1.02 | 186 |
| 5E | H₂N–⟨azetidine⟩–N(CH₃)–CH₂CH₂OCH₃ | 1-(2-aminoethyl)-N-(2-methoxyethyl)-N-methylazetidin-3-amine | A | 0.77 | 202 |

Intermediate 6A. N-(2-(3-(Benzyl(methyl)amino)pyrrolidin-1-yl)ethyl)-3-fluoropyridin-2-amine

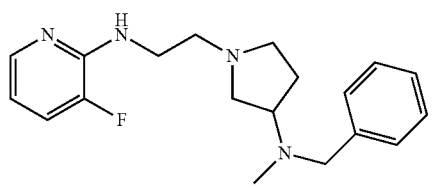 [SMILES: CN(Cc1ccccc1)C1CCN(CCNc2ncccc2F)C1]

1-(2-Aminoethyl)-N-benzyl-N-methylpyrrolidin-3-amine (INT 5A, 0.17 g, 0.73 mmol), Pd₂(dba)₃ (0.067 g, 0.07 mmol), 2,2'-bis(diphenylphosphino)-1,1'-binaphthyl (BI-NAP, 0.055 g, 0.087 mmol) and ᵗBuOK (0.210 g, 2.19 mmol) were added to a Raddley tube, under nitrogen, and dissolved in anhydrous THF (15 mL). 2-Bromo-3-fluoropyridine (0.135 g, 0.76 mmol) was added and the reaction mixture was stirred at 55° C. overnight. The solvents were evaporated and the residue was dissolved in EtOAc and aqueous sat NaHCO₃ solution. The aqueous layer was extracted with EtOAc and the combined organic layers were dried over Na₂SO₄, filtered and concentrated. The crude product thus obtained was purified by flash chromatography on neutral alumina, gradient CH:AcOEt from (100:0) to (80:20) to give the title compound as a solid (0.08 g, 34% yield).

HPLC-MS (Method A): Ret, 1.76 min; ESI+–MS m/z, 329 (M+1).

This method was used for the preparation of intermediates 6B-6G using suitable starting materials:

| INT | Structure | Chemical name | Method | Ret (min) | MS (M + H) |
|---|---|---|---|---|---|
| 6B | (phenyl)NH–CH₂CH₂–⟨pyrrolidine⟩–N(CH₃)–Bn | N-benzyl-N-methyl-1-(2-(phenylamino)ethyl)pyrrolidin-3-amine | A | 2.05 | 310 |
| 6C | F₃C–⟨pyridine⟩–NH–CH₂CH₂–⟨pyrrolidine⟩–N(CH₃)–Bn | N-(2-(3-(benzyl(methyl)amino)pyrrolidin-1-yl)ethyl)-6-(trifluoromethyl)pyridin-2-amine | A | 2.21 | 379 |
| 6D | F₃C–⟨pyridine⟩–NH–CH₂CH₂–⟨hexahydropyrrolo[3,4-c]pyrrole⟩–Bn | N-(2-(5-benzylhexahydropyrrolo[3,4-c]pyrrol-2(1H)-yl)ethyl)-6-(trifluoromethyl)pyridin-2-amine | A | 2.21 | 391 |
| 6E | F₃C–⟨pyridine⟩–NH–CH₂CH₂–⟨azetidine⟩–N(CH₃)–Bn | N-(2-(3-(benzyl(methyl)amino)azetidin-1-yl)ethyl)-6-(trifluoromethyl)pyridin-2-amine | A | 2.07 | 365 |

| INT | Structure | Chemical name | Method | Ret (min) | MS (M + H) |
|---|---|---|---|---|---|
| 6F | 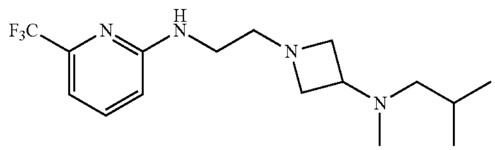 [SMILES: CC(C)CN(C)C1CN(CCNc2cccc(C(F)(F)F)n2)C1] | N-(2-(3-(isobutyl(methyl)amino)azetidin-1-yl)ethyl)-6-(trifluoromethyl)pyridin-2-amine | A | 2.11 | 331 |
| 6G | 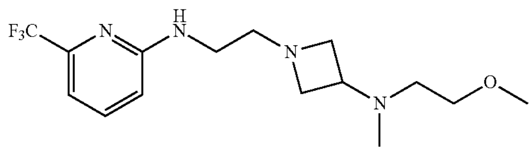 [SMILES: COCCN(C)C1CN(CCNc2cccc(C(F)(F)F)n2)C1] | N-(2-(3-((2-methoxyethyl)(methyl)amino)azetidin-1-yl)ethyl)-6-(trifluoromethyl)pyridin-2-amine | A | 1.67 | 347 |

Example 1. N-(2-(3-(Benzyl(methyl)amino)pyrrolidin-1-yl)ethyl)-N-(3-fluoropyridin-2-yl)propionamide

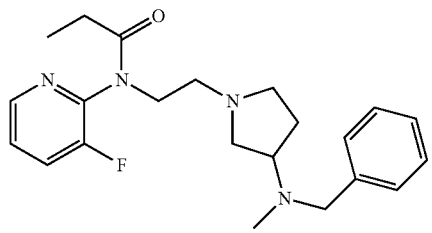 [SMILES: CCC(=O)N(CCN1CCC(N(C)Cc2ccccc2)C1)c1ncccc1F]

Propionyl chloride (78.5 µL, 0.616 mmol) was added to a solution of N-(2-(3-(benzyl(methyl)amino)pyrrolidin-1-yl)ethyl)-3-fluoropyridin-2-amine (INT 6A, 0.08 g, 0.205 mmol) and N-ethyl-N-isopropylpropan-2-amine (104.6 µL, 0.82 mmol) in DCE (10 mL) in a process vial under nitrogen atmosphere. The reaction mixture was heated under microwave irradiating conditions for 60 min at 80° C., after which it was allowed to reach rt. The reaction mixture was diluted with DCM (10 mL) and water (10 mL) was added. The aqueous phase was acidified with 10% HCl and the phases were separated. The organic phase was extracted with 10% HCl and the aqueous phase was made alkaline with 20% NaOH while cooling. AcOEt (10 mL) was added, the phases were separated and the aqueous phase was extracted with AcOEt. The combined organic phases were dried over Na₂SO₄, filtered and concentrated to give the title compound (0.076 g, yield 96%).

HPLC-MS (Method A): Ret, 1.74 min; ESI+–MS m/z, 385 (M+1).

This method was used for the preparation of example 2 using suitable starting materials:

The two enantiomers of example 2 were separated by Chiralpak IC column, flow rate 11 mL/min A: n-Heptane; B: (EtOH+0.33% DEA) 90/10, rt to give examples 3 and 4.

Example 5. N-(2-(3-(benzyl(methyl)amino)pyrrolidin-1-yl)ethyl)-N-(6-(trifluoromethyl)pyridin-2-yl)propionamide

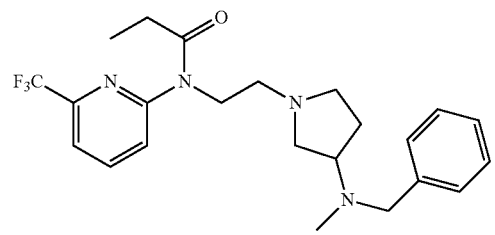 [SMILES: CCC(=O)N(CCN1CCC(N(C)Cc2ccccc2)C1)c1cccc(C(F)(F)F)n1]

Propionyl chloride (259 µL, 2.97 mmol) was added to a solution of N-(2-(3-(benzyl(methyl)amino)pyrrolidin-1-yl)ethyl)-6-(trifluoromethyl)pyridin-2-amine (INT 6B, 375 mg, 0.99 mmol) and N-ethyl-N-isopropylpropan-2-amine (690 µL, 3.96 mmol) in toluene (35 mL). The reaction mixture was stirred for 5 h at 85° C., after which it was allowed to reach rt. The reaction mixture was diluted with DCM (10 mL) and HCl 2N (10 mL) was added and the phases were separated. The organic phase was extracted with 2 N HCl and the aqueous phase was made alkaline with 20% aqueous NaOH solution, while cooling. AcOEt was added, the phases were separated and the aqueous phase was extracted with

| EX | Structure | Chemical name | Method | Ret (min) | MS (M + H) |
|---|---|---|---|---|---|
| 2 | 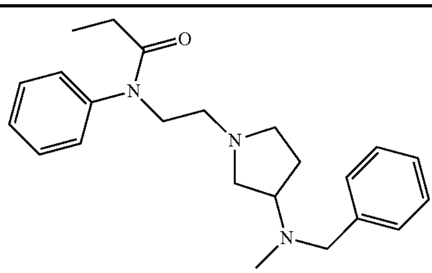 | N-(2-(3-(benzyl(methyl)amino)pyrrolidin-1-yl)ethyl)-N-phenylpropionamide | A | 2.01 | 366 |

AcOEt. The combined organic phases were dried over Na$_2$SO$_4$, filtered and concentrated to give the title compound (340 mg, yield 79%).

HPLC-MS (Method A): Ret, 2.18 min; ESI+-MS m/z, 435 (M+1).

The two enantiomers of example 5 were separated by Chiralpak IC column, flow rate 11 mL/min A: n-Heptane; B: (EtOH+0.33% DEA) 90/10, rt to give examples 6 and 7.

This acylacion method was used for the preparation of example 8, using INT 6D as starting material.

| EX | Structure | Chemical name | Method | Ret (min) | MS (M + H) |
|---|---|---|---|---|---|
| 8 | 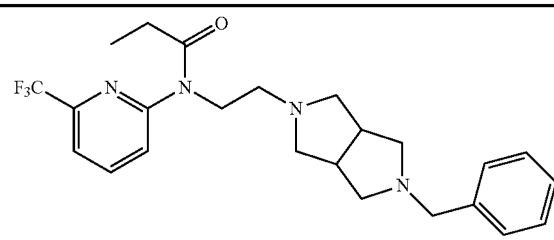 | N-(2-(5-benzylhexahydro-pyrrolo[3,4-c]pyrrol-2(1H)-yl)ethyl)-N-(6-(trifluoromethyl)pyridin-2-yl)propionamide | A | 2.18 | 448 |

Example 9. N-(2-(3-(benzyl(methyl)amino)azetidin-1-yl)ethyl)-N-(6-(trifluoromethyl)pyridin-2-yl)propionamide

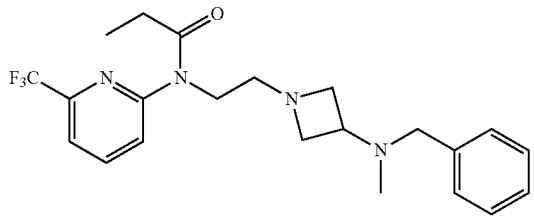 [SMILES: CCC(=O)N(CCN1CC(N(C)Cc2ccccc2)C1)c1cccc(C(F)(F)F)n1]

Propanoic anhydride (178 µL, 1.45 mmol) was added to a solution of N-(2-(3-(benzyl(methyl)amino)azetidin-1-yl)ethyl)-6-(trifluoromethyl)pyridin-2-amine (INT 6E, 176 mg, 0.48 mmol) in pyridine (7 mL) at 0° C. The reaction mixture was allowed to reach rt and stirred overnight. Then, volatiles were removed under vacuum and the crude was extracted in EtOAc washing with sat aqueous NaHCO$_3$ solution. The combined organic phases were dried over Na$_2$SO$_4$, filtered and concentrated. The crude product thus obtained was purified by flash chromatography on silica, gradient DCM/MeOH from (100:0) to (85:15) to give the title compound (80 mg, 39% yield).

HPLC-MS (Method A): Ret, 2.06 min; ESI+-MS m/z, 421 (M+1).

This acylacion method was used for the preparation of examples 10-11, using INT 6F and 6G as starting materials.

| EX | Structure | Chemical name | Method | Ret (min) | MS (M + H) |
|---|---|---|---|---|---|
| 10 | 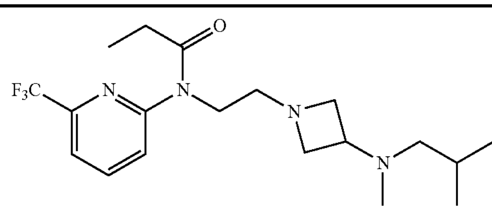 | N-(2-(3-(isobutyl(methyl)amino)azetidin-1-yl)ethyl)-N-(6-(trifluoromethyl)pyridin-2-yl)propionamide | A | 2.1 | 388 |
| 11 | 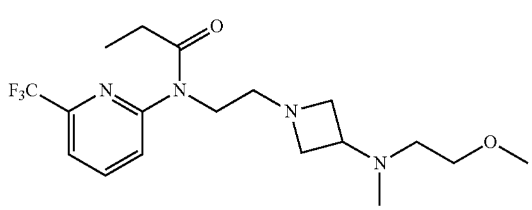 [SMILES: CCC(=O)N(CCN1CC(N(C)CCOC)C1)c1cccc(C(F)(F)F)n1] | N-(2-(3-((2-methoxyethyl)methyl)amino)azetidin-1-yl)ethyl)-N-(6-(trifluoromethyl)pyridin-2-yl)propionamide | A | 1.66 | 404 |

Example 12. N-(2-(3-(isobutyl(methyl)amino)pyrrolidin-1-yl)ethyl)-N-(6-(trifluoromethyl)pyridin-2-yl)propionamide

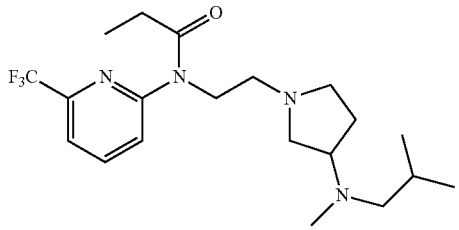 [SMILES: CCC(=O)N(CCN1CCC(N(C)CC(C)C)C1)c1cccc(C(F)(F)F)n1]

a) N-(2-(3-(methylamino)pyrrolidin-1-yl)ethyl)-N-(6-(trifluoromethyl)pyridin-2-yl)propionamide N-(2-(3-(benzyl(methyl)amino)pyrrolidin-1-yl)ethyl)-N-(6-(trifluoromethyl)pyridin-2-yl)propionamide (Example 5, 270 mg, 0.62 mmol) was dissolved in MeOH (20 mL) and ammonium formate (176 mg, 2.80 mmol) and Pd (55 mg, 20% Wt) was added. The suspension was stirred under N$_2$ atmosphere for 3 h at 65° C. The reaction mixture was filtered through celite, washed with MeOH and concentrated, to give the title compound (186 mg, yield 87%).

HPLC-MS (Method A): Ret, 1.31 min; ESI$^+$–MS m/z, 345 (M+1).

b) Title Compound

1-Bromo-2-methylpropane (125 μL, 1.15 mmol) was added to a solution the compound obtained in the previous step (99 mg, 0.28 mmol) and K$_2$CO$_3$ (119 mg, 0.86 mmol) in ACN (12 mL). The reaction mixture was stirred at 70° C. for 48 h and then it was cooled down to rt. AcOEt and sat aqueous NaHCO$_3$ solution were added and the phases were separated. The organic layer was dried over Na$_2$SO$_4$, filtered and concentrated to give the title compound (66 mg, yield 57%).

HPLC-MS (Method A): Ret, 2.06 min; ESI+–MS m/z, 401 (M+1).

The two enantiomers of example 12 were separated by Chiralpak IC column, flow rate 11 mL/min A: n-Heptane; B: (EtOH+0.33% DEA) 90/10, rt to give examples 13 and 14.

This method and the subsequent chiral HPLC separation was used for the preparation of example 15 and its corresponding enantiomers examples 16 and 17

Example 18. N-(2-(5-isobutylhexahydropyrrolo[3,4-c]pyrrol-2(1H)-yl)ethyl)-N-(6-(trifluoromethyl)pyridin-2-yl)propionamide

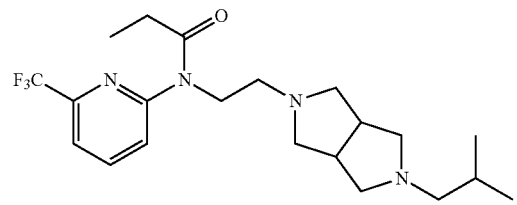 [SMILES: CCC(=O)N(CCN1CC2CN(CC(C)C)CC2C1)c1cccc(C(F)(F)F)n1]

a) N-(2-(hexahydropyrrolo[3,4-c]pyrrol-2(1H)-yl)ethyl)-N-(6-(trifluoromethyl)pyridin-2-yl)propionamide N-(2-(5-benzylhexahydropyrrolo[3,4-c]pyrrol-2(1H)-yl)ethyl)-N-(6-(trifluoromethyl)pyridin-2-yl)propionamide (Example 8, 760 mg, 1.7 mmol) was dissolved in DCE (10 mL) and chloroethyl chloroformate (487 mg, 3.4 mmol) was added. The mixture was stirred for 16 h at 85° C. Then, volatiles were removed under vacuum and MeOH (8 mL) was added and stirred at the reflux temperature for 2 h. The crude mixture was concentrated to give the title compound (174 mg, yield 51%), that was used in the next step without further purification.

HPLC-MS (Method A): Ret, 1.36 min; ESI+–MS m/z, 357 (M+1).

b) Title Compound

The title compound was obtained following the method described for example 8 step b.

HPLC-MS (Method A): Ret, 1.99 min; ESI+–MS m/z, 414 (M+1).

| EX | Structure | Chemical name | Method | Ret (min) | MS (M + H) |
|---|---|---|---|---|---|
| 15 | ![structure] | N-(2-(3-((2-ethoxyethyl)(methyl)amino)pyrrolidin-1-yl)ethyl)-N-(6-(trifluoromethyl)pyridin-2-yl)propionamide | A | 3.58 | 418 |

This method was used for the preparation of example 19:

| EX | Structure | Chemical name | Method | Ret (min) | MS (M + H) |
|----|-----------|---------------|--------|-----------|------------|
| 19 | ![structure] | N-(2-(5-(2-ethoxyethyl)hexahydropyrrolo[3,4-c]pyrrol-2(1H)-yl)ethyl)-N-(6-(trifluoromethyl)pyridin-2-yl)propionamide | A | 1.76 | 430 |

Table of Examples with Binding to the μ-Opioid Receptor and the $\sigma_1$-Receptor:
Biological Activity
Pharmacological Study
Human $\sigma_1$ Receptor Radioligand Assay To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail
Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opioid receptor it is a very preferred embodiment in which the compounds are selected which act as dual ligands of the $\sigma_1$ receptor and the μ-opioid receptor and especially compounds which have a binding expressed as $K_i$ which is preferably <1000 nM for both receptors, more preferably <500 nM, even more preferably <100 nM.

The following scale as been adopted for representing the binding to the the $\sigma_1$ receptor and the μ-opioid receptor expressed as $K_i$:
+ Both $K_i$-μ and $K_i$-$\sigma_1$ >=500 nM
++ One $K_i$<500 nM while the other $K_i$ is >=500 nM
+++ Both $K_i$-μ and $K_i$-$\sigma_1$<500 nM
++++ Both $K_i$-μ and $K_1$-$\sigma_1$<100 nM All compounds prepared in the present application exhibit binding to the $\sigma_1$ receptor and the μ-opioid receptor, in particular the following binding results are shown:

| EX | μ and $\sigma_1$ dual binding |
|----|-------------------------------|
| 1  | ++  |
| 2  | +++ |
| 3  | ++  |
| 4  | +++ |
| 5  | +   |
| 6  | ++  |
| 7  | +++ |
| 8  | ++  |
| 9  | ++  |
| 10 | ++  |
| 11 | +   |
| 12 | +   |
| 13 | +   |
| 14 | +   |
| 15 | +   |
| 16 | +   |
| 17 | +   |
| 18 | ++  |
| 19 | ++  |

The invention claimed is:
1. A compound of Formula (I):

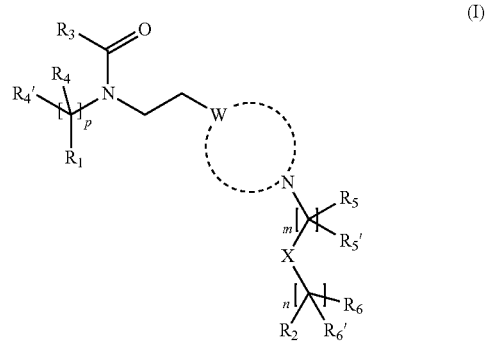

wherein
m is 1 or 2;
n is 0, 1 or 2;
p is 0, 1 or 2;
X is a bond, —C($R_x R_{x'}$)—, C=O or —O—;
  wherein $R_x$ is selected from the group consisting of halogen, —$OR_8$, substituted or unsubstituted $C_{1-6}$ alkyl, substituted or unsubstituted C$_{2-6}$ alkenyl and substituted or unsubstituted C$_{2-6}$ alkynyl;

R$_{x'}$ is selected from the group consisting of hydrogen, halogen, substituted or unsubstituted C$_{1-6}$ alkyl, substituted or unsubstituted C$_{2-6}$ alkenyl and substituted or unsubstituted C$_{2-6}$ alkynyl;

R$_8$ is selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

W is nitrogen or carbon;

R$_1$ is selected from the group consisting of substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;

wherein the cycloalkyl, aryl or heterocyclyl in R$_1$, if substituted, is substituted with one or more substituents selected from the group consisting of halogen, —R$_{11}$, —OR$_{11}$, —NO$_2$; NR$_{11}$R$_{11'''}$, NR$_{11}$C(O)R$_{11'}$—, —NR$_{11}$S(O)$_2$R$_{11'}$, —S(O)$_2$NR$_{11}$R$_{11'}$, —NR$_{11}$C(O)NR$_{11'}$R$_{11'''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —NR$_{11}$S(O)$_2$NR$_{11'}$R$_{11''}$ and —C(CH$_3$)$_2$OR$_{11}$;

and wherein the cycloalkyl or non-aromatic heterocyclyl in R$_1$, if substituted, may also be substituted with

or =O;

wherein the alkyl, alkenyl or alkynyl in R$_1$, if substituted, is substituted with one or more substituent/s selected from the group consisting of —OR$_{11}$, halogen, —CN, haloalkyl, haloalkoxy, —SR$_{11}$, —S(O)R$_{11}$, and —S(O)$_2$R$_{11}$;

wherein R$_{11}$, R$_{11'}$ and R$_{11''}$ are independently selected from the group consisting of hydrogen, unsubstituted C$_{1-6}$ alkyl, unsubstituted C$_{2-6}$ alkenyl and unsubstituted C$_{2-6}$ alkynyl;

and wherein R$_{11'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

R$_2$ is selected from the group consisting of hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl, wherein said cycloalkyl, aryl or heterocyclyl in R$_2$, if substituted, is substituted with one or more substituent/s selected from halogen, —R$_{12}$, —OR$_{12}$—NO$_2$—NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, —NR$_{12}$S(O)$_2$NR$_{12'}$R$_{12''}$ and C(CH$_3$)$_2$OR$_{12}$;

and wherein the cycloalkyl or non-aromatic heterocyclyl in R$_2$, if substituted, may also be substituted with

or =O;

wherein the alkyl, alkenyl or alkynyl in R$_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;

wherein R$_{12}$, R$_{12'}$ and R$_{12''}$ are independently selected from hydrogen, unsubstituted C$_{1-6}$ alkyl unsubstituted C$_{2-6}$ alkenyl and unsubstituted C$_{2-6}$ alkynyl;

and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;

R$_3$ is selected from the group consisting of substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —NR$_7$R$_{7'}$, and —CH$_2$OR$_7$;

wherein R$_7$ and R$_{7'}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

R$_4$ and R$_{4'}$ are independently selected from the group consisting of hydrogen, substituted or unsubstituted C$_{1-6}$ alkyl, substituted or unsubstituted C$_{2-5}$ alkenyl and substituted or unsubstituted C$_{2-6}$ alkynyl, R$_5$ and R$_{5'}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

R$_6$ and R$_{6'}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

and wherein

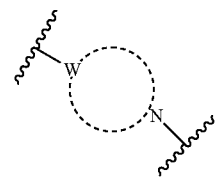

is selected from the group consisting of

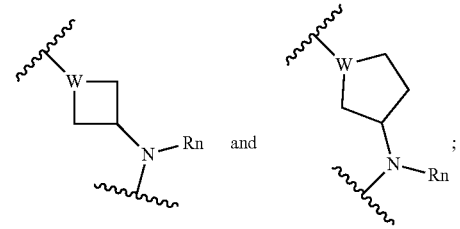

wherein Rn is selected from the group consisting of unsubstituted C$_{1-6}$ alkyl, unsubstituted C$_{2-6}$ alkenyl and unsubstituted C$_{2-6}$ alkynyl;

wherein the alkyl, alkenyl or alkynyl, other than those defined in R$_1$ or R$_2$, if substituted, is substituted with one or more substituent/s selected from the group consisting of —OR$_{13}$, halogen, —CN, haloalkyl, haloalkoxy, —SR$_{13}$, —S(O)R$_{13}$, and —S(O)$_2$R$_{13}$;

wherein $R_{13}$ is selected from the group consisting of hydrogen, unsubstituted $C_{1-6}$ alkyl, unsubstituted $C_{2-6}$ alkenyl, and unsubstituted $C_{2-6}$ alkynyl;

wherein the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_2)_2OR_{14}$;

and wherein the cycloalkyl or non-aromatic heterocyclyl, other than those defined in $R_1$ or $R_2$, if substituted, may also be substituted with

or =O;

wherein $R_{14}$, $R_{14''}$ and $R_{14'''}$ are independently selected from hydrogen, unsubstituted $C_{1-6}$ alkyl, unsubstituted $C_{2-6}$, alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc:

optionally as a stereoisomer, including enantiomers and diastereomers, a racemate or a mixture of at least two stereoisomers, including enantiomers and/or diastereomers, in any mixing ratio, or a corresponding salt thereof.

2. The compound according to claim 1, wherein

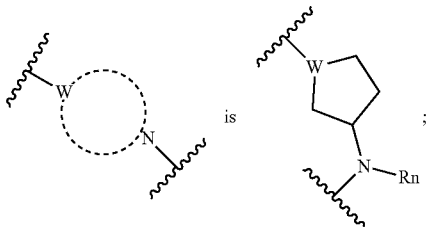 is

W is nitrogen or carbon; and Rn is selected from unsubstituted $C_{1-6}$ alkyl, unsubstituted $C_{2-6}$ alkenyl and unsubstituted $C_{2-6}$ alkynyl.

3. The compound according to claim 2, wherein W is nitrogen and Rn is unsubstituted $C_{1-6}$ alkyl.

4. The compound according to claim 1, wherein the compound is a compound of formula (I')

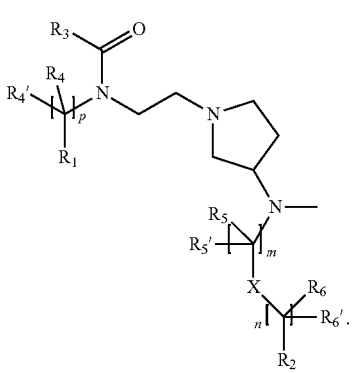

5. The compound according to claim 1, wherein X is a bond or —O.

6. The compound according to claim 5, wherein X is a bond; and/or
m is 1; and/or
n is 0; and/or
p is 0.

7. The compound according to claim 1, wherein the compound
is a compound of Formula (I²')

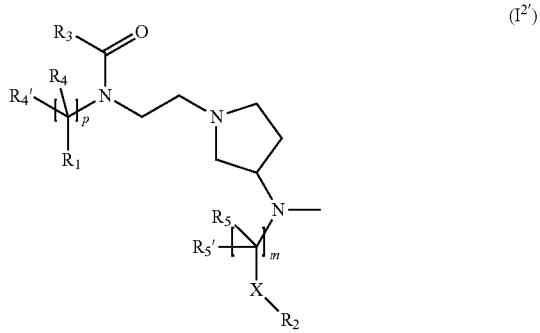

wherein
X is a bond, C=O or —O—;
m is 1 or 2; and
p is 0, 1 or 2.

8. The compound according to claim 7, wherein
X is a bond;
m is 1; and
p is 0.

9. The compound according to claim 1, wherein the compound
is a compound of Formula (I³')

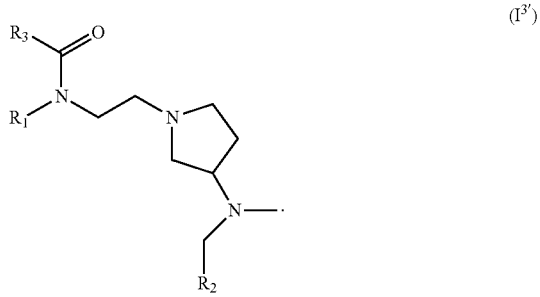

10. The compound according to claim 1, wherein $R_1$ is selected from the group consisting of substituted or unsubstituted cycloalkyl, substituted or unsubstituted aryl and substituted or unsubstituted heterocyclyl.

11. The compound according to claim 10, wherein $R_1$ is substituted or unsubstituted phenyl or substituted or unsubstituted pyridine.

12. The compound according to claim 1, wherein
$R_2$ is selected from hydrogen, substituted or unsubstituted $C_{1-6}$ alkyl, and substituted or unsubstituted aryl.

13. The compound according to claim 12, wherein $R_2$ is substituted or unsubstituted phenyl.

14. The compound according claim 1, wherein
$R_3$ is substituted or unsubstituted $C_{1-6}$ alkyl.

15. The compound according to claim 14, wherein $R_3$ is unsubstituted ethyl.

16. The compound according to claim 1, wherein $R_4$ and $R_4'$ are independently selected from hydrogen and substituted or unsubstituted $C_{1-6}$ alkyl.

17. The compound according to claim 1, wherein $R_5$ and $R_5'$ are independently selected from hydrogen and substituted or unsubstituted $C_{1-6}$ alkyl.

18. The compound according to claim 17, wherein $R_5$ and $R_5'$ are both hydrogen.

19. The compound according to claim 1, wherein the compound is selected from the group consisting of:
N-(2-(3-(benzyl(methyl)amino)pyrrolidin-1-yl)ethyl)-N-(3-fluoropyridin-2-yl)propionamide
N-(2-(3-(benzyl(methyl)amino)pyrrolidin-1-yl)ethyl)-N-phenylpropionamide
(S)—N-(2-(3-(benzyl(methyl)amino)pyrrolidin-1-yl) ethyl)-N-phenylpropionamide
(R)—N-(2-(3-(benzyl(methyl)amino)pyrrolidin-1-yl) ethyl)-N-phenylpropionamide
optionally as a stereoisomer, including enantiomers and diastereomers, a racemate or a mixture of at least two stereoisomers, including enantiomers and/or diastereomers, in any mixing ratio, or a corresponding salt thereof.

20. The compound according to claim 1, wherein the compound is selected from the group consisting of:
N-(2-(3-(benzyl(methyl)amino)pyrrolidin-1-yl)ethyl)-N-(6-(trifluoromethyl)pyridin-2-yl)propionamide
Enantiomer of N-(2-(3-(benzyl(methyl)amino)pyrrolidin-1-yl)ethyl)-N-(6-(trifluoromethyl)pyridin-2-yl)propionamide
N-(2-(3-(benzyl(methyl)amino)azetidin-1-yl)ethyl)-N-(6-(trifluoromethyl)pyridin-2-yl)propionamide
N-(2-(3-(isobutyl(methyl)amino)azetidin-1-yl)ethyl)-N-(6-(trifluoromethyl)pyridin-2-yl)propionamide
N-(2-(3-((2-methoxyethyl)(methyl)amino)azetidin-1-yl) ethyl)-N-(6-(trifluoromethyl)pyridin-2-yl)propionamide
N-(2-(3-(isobutyl(methyl)amino)pyrrolidin-1-yl)ethyl)-N-(6-(trifluoromethyl)pyridin-2-yl)propionamide
Enantiomer of N-(2-(3-(isobutyl(methyl)amino)pyrrolidin-1-yl)ethyl)-N-(6-(trifluoromethyl)pyridin-2-yl) propionamide
N-(2-(3-((2-ethoxyethyl)(methyl)amino)pyrrolidin-1-yl) ethyl)-N-(6-(trifluoromethyl)pyridin-2-yl)propionamide
Enantiomer of N-(2-(3-((2-ethoxyethyl)(methyl)amino) pyrrolidin-1-yl)ethyl)-N-(6-(trifluoromethyl)pyridin-2-yl)propionamide
optionally as a stereoisomer, including enantiomers and diastereomers, a racemate or a mixture of at least two stereoisomers, including enantiomers and/or diastereomers, in any mixing ratio, or a corresponding salt thereof.

21. A process for the preparation of the compound of Formula (I) as defined in claim 1, wherein the process comprises reacting a compound of Formula VII

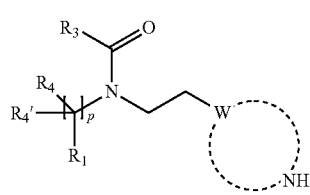

VII with a compound of formula VIIIa through an alkylaton reaction or VIIIb through a reductive amination reaction

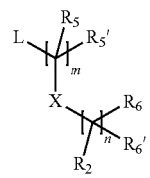

VIIIa

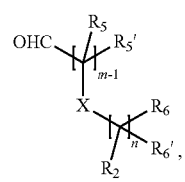

VIIIb or
wherein the process comprises an acylation of a compound of Formula IVb

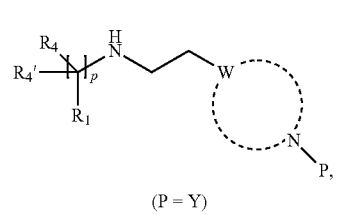

IVb wherein Y is

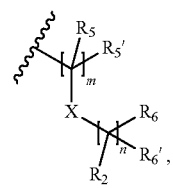

with a compound of formula Va or Vb

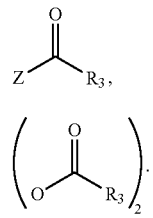

Va

Vb wherein

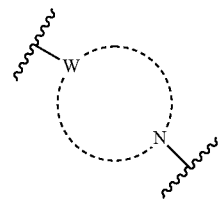

is selected from the group consisting of

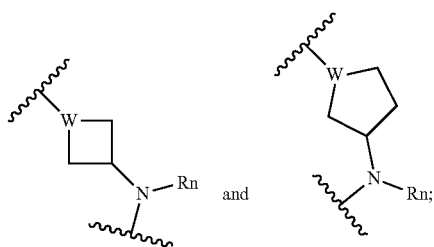

and wherein L is a leaving group selected from the group consisting of halogen, mesylate, tosylate and triflate, and wherein Z is chloro, bromo, hydroxy, methoxy or ethoxy.

22. A process for the preparation of a compound of Formula (I) according to claim 1, employing a compound of Formula IIa, IIb, III, IVa, IVb, Va, Vb, VI, VII, VIIIa or VIIIb

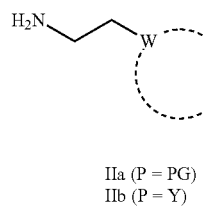

IIa (P = PG)
IIb (P = Y)

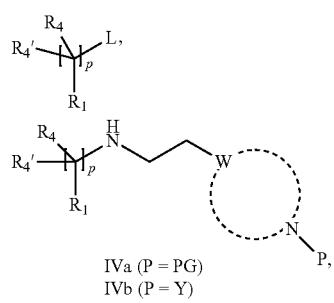

IVa (P = PG)
IVb (P = Y)

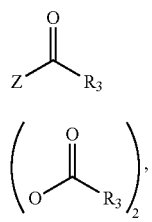

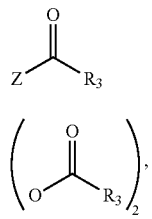

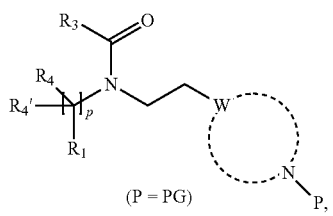

(P = PG)

VI

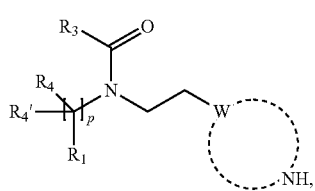

VII

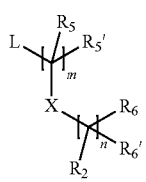

VIIIa

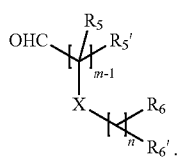

VIIIb wherein

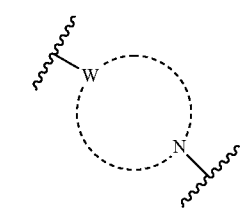

III is selected from the group consisting of

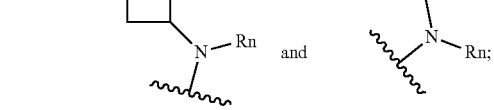

Va

Vb wherein L is a leaving group selected from the group consisting of halogen, mesylate, tosylate and triflate, wherein Z is chloro, bromo, hydroxy, methoxy or ethoxy;

wherein Y is

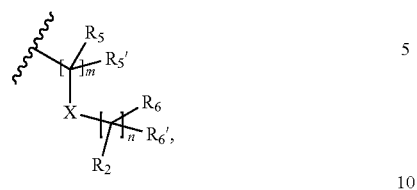

and
wherein PG is a protecting group selected from the group consisting of benzyl and tert-butoxycarbonyl.

23. A pharmaceutical composition which comprises the compound according to claim 1, or a pharmaceutically acceptable salt thereof, and a pharmaceutically acceptable carrier, adjuvant or vehicle.

24. A method of treating pain in a subject in need thereof, comprising administration of an effective amount of the compound according to claim 1.

25. The method according to claim 24, wherein the pain is selected from the group consisting of medium to severe pain, visceral pain, chronic pain, cancer pain, migraine, inflammatory pain, acute pain, neuropathic pain, allodynia, and hyperalgesia.

* * * * *

UNITED STATES PATENT AND TRADEMARK OFFICE
CERTIFICATE OF CORRECTION

| | |
|---|---|
| PATENT NO. | : 10,351,549 B2 |
| APPLICATION NO. | : 15/747220 |
| DATED | : July 16, 2019 |
| INVENTOR(S) | : Monica Garcia-Lopez and Carmen Almansa-Rosales |

It is certified that error appears in the above-identified patent and that said Letters Patent is hereby corrected as shown below:

On the Title Page

Item (56) under OTHER PUBLICATIONS, "Pharmacoi" should read -- Pharmacol --.

In the Claims

Column 81, Line 12: "C(CH$_2$)" should read -- C(CH$_3$) --.

Column 81, Line 19: "R$_{14''}$" should read -- R$_{14'}$ --.

Column 81, Line 22: "C$_{2-6}$," should read -- C$_{2-6}$ --.

Signed and Sealed this
Fourteenth Day of January, 2020

Andrei Iancu
*Director of the United States Patent and Trademark Office*